US012799483B2

(12) United States Patent
Sleiman et al.

(10) Patent No.: US 12,799,483 B2
(45) Date of Patent: Nov. 17, 2026

(54) DNA-ENCODED FUNCTIONALIZED APTAMERS

(71) Applicant: THE ROYAL INSTITUTION FOR THE ADVANCEMENT OF LEARNING/MCGILL UNIVERSITY, Montréal (CA)

(72) Inventors: Hanadi Sleiman, Montreal West (CA); Donatien Philippe Marie Lacroix De Vimeur De Rochambeau, Montréal (CA); Maureen Mckeague, Mont-Royal (CA); Serhii Hirka, Montréal (CA); Daniel Saliba, Montreal (CA); Shaun Ian Anderson, Montreal (CA)

(73) Assignee: THE ROYAL INSTITUTION FOR THE ADVANCEMENT OF LEARNING / MCGILL UNIVERSITY, Room Montréal QC (CA)

( * ) Notice: Subject to any disclaimer, the term of this patent is extended or adjusted under 35 U.S.C. 154(b) by 810 days.

(21) Appl. No.: 18/001,023

(22) PCT Filed: Jun. 30, 2021

(86) PCT No.: PCT/CA2021/050899

§ 371 (c)(1),
(2) Date: Dec. 7, 2022

(87) PCT Pub. No.: WO2022/000087

PCT Pub. Date: Jan. 6, 2022

(65) Prior Publication Data

US 2023/0220381 A1 Jul. 13, 2023

Related U.S. Application Data

(60) Provisional application No. 63/045,938, filed on Jun. 30, 2020.

(51) Int. Cl.

| | |
|---|---|
| ***C12N 15/11*** | (2006.01) |
| ***C07H 19/06*** | (2006.01) |
| ***C12N 15/10*** | (2006.01) |
| ***C12N 15/115*** | (2010.01) |

(52) U.S. Cl.
CPC ............ *C12N 15/111* (2013.01); *C07H 19/06* (2013.01); *C12N 15/1093* (2013.01); *C12N 15/115* (2013.01); *C12N 2310/16* (2013.01); *C12N 2310/314* (2013.01); *C12N 2330/31* (2013.01)

(58) Field of Classification Search
CPC . C12N 15/111; C12N 15/1093; C12N 15/115; C12N 2310/16; C12N 2310/314; C12N 2330/31; C40B 40/06; C40B 50/14
See application file for complete search history.

(56) References Cited

PUBLICATIONS

Lyttle, Matthew H., et al. "New reagents and methods for the synthesis of internal and 3'-labeled DNA." Bioconjugate chemistry 13.5 (2002): 1146-1154. (Year: 2002).*
de Rochambeau thesis(Lacroix de Vimeur de Rochambeau, Donatien. "Expanding the scope of sequence-defined Oligo (Phosphodiester) s with novel building blocks." (2019).; available May 2019). (Year: 2019).*
International Search Report of PCT/CA2021/050899—WO 2022/000087 A1.
Lyttle, M.H. et al. New Reagents and Methods for the Synthesis ofInternal and 3'-Labeled DNA. Bioconjugate Chemistry, Jul. 19, 2002 (Jul. 19, 2002), vol. 13, pp. 1146-1154.
Ouahabi et al. Synthesis of Non-Natural Sequence-Encoded Polymers Using Phosphoramidite Chemistry. The Journal of the American Chemical Society, Apr. 8, 2015 (Aug. 4, 2015), vol. 137, pp. 5629-5635.
Wang et al. Modularly Engineered Solid-Phase Synthesis of Aptamer-Functionalized Small Molecule Drugs for Targeted Cancer Therapy. Advanced Therapeutics, Jun. 21, 2020 (Jun. 21, 2020), vol. 3, 2000074.
Meini et al. A sensitive and selective thrombin impedimetric aptasensor based on tailored aptamers obtained by solid-phase synthesis. Sensors and Actuators B:Chemical, Mar. 23, 2012 (Mar. 23, 2012), vol. 166-167, pp. 715-720.

* cited by examiner

*Primary Examiner* — Sahana S Kaup
(74) *Attorney, Agent, or Firm* — Norton Rose Fulbirght Canada

(57) ABSTRACT

It is provided the synthesis of an aptamer-like encoded oligomer (ALEnOmer), method of producing same and method of preparing a library of ALEnOmes. More particularly, the method of preparing ALEnOmer comprises coupling at least one phosphoramidite monomer with an orthogonal protecting group, and the ALEnOmer produces comprises a DNA coding strand covalently attached to an oligomer through a branching unit, wherein the oligomer has a degree of polymerization at least 5 and is an aptamer.

12 Claims, 8 Drawing Sheets

Specification includes a Sequence Listing.

SEQUENCE LISTING

<160> NUMBER OF SEQ ID NOS: 28

<210> SEQ ID NO 1
<211> LENGTH: 19
<212> TYPE: DNA
<213> ORGANISM: Artificial Sequence
<220> FEATURE:
<223> OTHER INFORMATION: AT

<400> SEQUENCE: 1
tttttcagtt gaccatata 19

<210> SEQ ID NO 2
<211> LENGTH: 47
<212> TYPE: DNA
<213> ORGANISM: Artificial Sequence
<220> FEATURE:
<223> OTHER INFORMATION: HYD1

<400> SEQUENCE: 2
acgacgacga cgacgacgac gacgacgacg acgacgacga cgacgcg 47

<210> SEQ ID NO 3
<211> LENGTH: 20
<212> TYPE: DNA
<213> ORGANISM: Artificial Sequence
<220> FEATURE:
<223> OTHER INFORMATION: LEV1

<400> SEQUENCE: 3
tttttttttg ttcctaaccg 20

<210> SEQ ID NO 4
<211> LENGTH: 14
<212> TYPE: DNA

-continued

<213> ORGANISM: Artificial Sequence
<220> FEATURE:
<223> OTHER INFORMATION: LEV2

<400> SEQUENCE: 4 tttttttgt tccg 14

<210> SEQ ID NO 5
<211> LENGTH: 18
<212> TYPE: DNA
<213> ORGANISM: Artificial Sequence
<220> FEATURE:
<223> OTHER INFORMATION: T10

<400> SEQUENCE: 5
ggtcctaatg ccgatcga 18

<210> SEQ ID NO 6
<211> LENGTH: 18
<212> TYPE: DNA
<213> ORGANISM: Artificial Sequence
<220> FEATURE:
<223> OTHER INFORMATION: T30

<400> SEQUENCE: 6
ggtcctaatg ccgatcga 18

<210> SEQ ID NO 7
<211> LENGTH: 22
<212> TYPE: DNA
<213> ORGANISM: Artificial Sequence
<220> FEATURE:
<223> OTHER INFORMATION: DNA 21mer
<220> FEATURE:
<221> NAME/KEY: misc_feature
<222> LOCATION: (19)...(19)
<223> OTHER INFORMATION: from x 20 hydrazine treatments of 10 min
<220> FEATURE:
<221> NAME/KEY: misc_feature
<222> LOCATION: (19)...(19)
<223> OTHER INFORMATION: n = a, c, t or g

<400> SEQUENCE: 7
tttttcagtt gaccatatna at 22

<210> SEQ ID NO 8
<211> LENGTH: 48
<212> TYPE: DNA
<213> ORGANISM: Artificial Sequence
<220> FEATURE:
<223> OTHER INFORMATION: BR1

<400> SEQUENCE: 8
cgtcgaggcc cgggaagaaa ggatcgaaca cgtcacgcct tttttttt 48

<210> SEQ ID NO 9
<211> LENGTH: 45
<212> TYPE: DNA
<213> ORGANISM: Artificial Sequence
<220> FEATURE:
<223> OTHER INFORMATION: BR2

<400> SEQUENCE: 9
cgtcgaggcc cgggaagaaa tcgagcatag gatacacgtc acgcc 45

<210> SEQ ID NO 10
<211> LENGTH: 66

<212> TYPE: DNA
<213> ORGANISM: Artificial Sequence
<220> FEATURE:
<223> OTHER INFORMATION: BR3

<400> SEQUENCE: 10
cgtcgaggcc cttaattggt tccttaacct taggatatgt ctactacacg tcacgccttt 60
tttttt 66

<210> SEQ ID NO 11
<211> LENGTH: 77
<212> TYPE: DNA
<213> ORGANISM: Artificial Sequence
<220> FEATURE:
<223> OTHER INFORMATION: TBA1

<400> SEQUENCE: 11
cgtcgaggcc ccttcttctt cgtcttcttc ttaggaggtt ggtgtggttg gtttttacac 60
gtcacgcctt ttttttt 77

<210> SEQ ID NO 12
<211> LENGTH: 77
<212> TYPE: DNA
<213> ORGANISM: Artificial Sequence
<220> FEATURE:
<223> OTHER INFORMATION: TBA2
<220> FEATURE:
<221> NAME/KEY: misc_feature
<222> LOCATION: (39)...(39)
<223> OTHER INFORMATION: n = unknown nucleotide
<220> FEATURE:
<221> NAME/KEY: misc_feature
<222> LOCATION: (43)...(43)
<223> OTHER INFORMATION: n = unknown nucleotide
<220> FEATURE:
<221> NAME/KEY: misc_feature
<222> LOCATION: (48)...(48)
<223> OTHER INFORMATION: n = unknown nucleotide

<400> SEQUENCE: 12
cgtcgaggcc cgtgcttacc cgtgaccttc ttaggaggnt ggngtggntg gtttttacac 60
gtcacgcctt ttttttt 77

<210> SEQ ID NO 13
<211> LENGTH: 76
<212> TYPE: DNA
<213> ORGANISM: Artificial Sequence
<220> FEATURE:
<223> OTHER INFORMATION: TBA3
<220> FEATURE:
<221> NAME/KEY: misc_feature
<222> LOCATION: (39)...(39)
<223> OTHER INFORMATION: n = unknown nucleotide
<220> FEATURE:
<221> NAME/KEY: misc_feature
<222> LOCATION: (40)...(40)
<223> OTHER INFORMATION: n = unknown nucleotide
<220> FEATURE:
<221> NAME/KEY: misc_feature
<222> LOCATION: (43)...(43)
<223> OTHER INFORMATION: n = unknown nucleotide
<220> FEATURE:
<221> NAME/KEY: misc_feature
<222> LOCATION: (44)...(44)
<223> OTHER INFORMATION: n = unknown nucleotide
<220> FEATURE:
<221> NAME/KEY: misc_feature
<222> LOCATION: (48)...(48)
<223> OTHER INFORMATION: n = unknown nucleotide
<220> FEATURE:

<221> NAME/KEY: misc_feature
<222> LOCATION: (52)...(52)
<223> OTHER INFORMATION: n = unknown nucleotide

<400> SEQUENCE: 13
cgtcgaggcc catacaggta taatgccatt gaaggaggnn ggnntggnag gntttacacg 60
tcacgccttt tttttt 76

<210> SEQ ID NO 14
<211> LENGTH: 75
<212> TYPE: DNA
<213> ORGANISM: Artificial Sequence
<220> FEATURE:
<223> OTHER INFORMATION: TBA1F

<400> SEQUENCE: 14
cgtcgaggcc ccttcttctt cgtcttcttc ttaggaggtg gtgtggttgg ttttacacgt 60
cacgcctttt ttttt 75

<210> SEQ ID NO 15
<211> LENGTH: 77
<212> TYPE: DNA
<213> ORGANISM: Artificial Sequence
<220> FEATURE:
<223> OTHER INFORMATION: TBA2F
<220> FEATURE:
<221> NAME/KEY: misc_feature
<222> LOCATION: (43)...(43)
<223> OTHER INFORMATION: n = unknown nucleotide
<220> FEATURE:
<221> NAME/KEY: misc_feature
<222> LOCATION: (48)...(48)
<223> OTHER INFORMATION: n = unknown nucleotide

<400> SEQUENCE: 15
cgtcgaggcc cgtgcttacc cgtgaccttc ttaggaggtt ggngtggntg gtttttacac 60
gtcacgcctt ttttttt 77

<210> SEQ ID NO 16
<211> LENGTH: 76
<212> TYPE: DNA
<213> ORGANISM: Artificial Sequence
<220> FEATURE:
<223> OTHER INFORMATION: TBA3F
<220> FEATURE:
<221> NAME/KEY: misc_feature
<222> LOCATION: (39)...(39)
<223> OTHER INFORMATION: n = unknown nucleotide
<220> FEATURE:
<221> NAME/KEY: misc_feature
<222> LOCATION: (40)...(40)
<223> OTHER INFORMATION: n = unknown nucleotide
<220> FEATURE:
<221> NAME/KEY: misc_feature
<222> LOCATION: (43)...(43)
<223> OTHER INFORMATION: n = unknown nucleotide
<220> FEATURE:
<221> NAME/KEY: misc_feature
<222> LOCATION: (44)...(44)
<223> OTHER INFORMATION: n = unknown nucleotide
<220> FEATURE:
<221> NAME/KEY: misc_feature
<222> LOCATION: (48)...(48)
<223> OTHER INFORMATION: n = unknown nucleotide
<220> FEATURE:
<221> NAME/KEY: misc_feature
<222> LOCATION: (52)...(52)
<223> OTHER INFORMATION: n = unknown nucleotide

<400> SEQUENCE: 16

-continued cgtcgaggcc cacgcaggta taatgccatt gaaggaggnn ggnntggnag gntttacacg 60
tcacgccttt tttttt 76

<210> SEQ ID NO 17
<211> LENGTH: 33
<212> TYPE: DNA
<213> ORGANISM: Artificial Sequence
<220> FEATURE:
<223> OTHER INFORMATION: forward primer

<400> SEQUENCE: 17
acactgacga catggttcta cacgtcgagg ccc 33

<210> SEQ ID NO 18
<211> LENGTH: 39
<212> TYPE: DNA
<213> ORGANISM: Artificial Sequence
<220> FEATURE:
<223> OTHER INFORMATION: reverse primer

<400> SEQUENCE: 18
tacggtagca gagacttggt ctggcgtgac gtgtatcct 39

<210> SEQ ID NO 19
<211> LENGTH: 58
<212> TYPE: DNA
<213> ORGANISM: Artificial Sequence
<220> FEATURE:
<223> OTHER INFORMATION: LIB
<220> FEATURE:
<221> NAME/KEY: misc_feature
<222> LOCATION: (12)...(32)
<223> OTHER INFORMATION: n = A, C, G or T
<220> FEATURE:
<221> NAME/KEY: misc_feature
<222> LOCATION: (37)...(37)
<223> OTHER INFORMATION: n = unknown nucleotide

<400> SEQUENCE: 19
cgtcgaggcc cnnnnnnnnn nnnnnnnnnn nnagganaca cgtcacgcct tttttttt 58

<210> SEQ ID NO 20
<211> LENGTH: 15
<212> TYPE: DNA
<213> ORGANISM: Artificial Sequence
<220> FEATURE:
<223> OTHER INFORMATION: PC

<400> SEQUENCE: 20
ggttggtgtg gttgg 15

<210> SEQ ID NO 21
<211> LENGTH: 15
<212> TYPE: DNA
<213> ORGANISM: Artificial Sequence
<220> FEATURE:
<223> OTHER INFORMATION: NCS

<400> SEQUENCE: 21
ggttggtgtt gtttg 15

<210> SEQ ID NO 22
<211> LENGTH: 58
<212> TYPE: DNA
<213> ORGANISM: Artificial Sequence
<220> FEATURE:

-continued

<223> OTHER INFORMATION: NCL

<400> SEQUENCE: 22
cgtcgaggcc ccttcttctt cgtcttcttc ttaggataca cgtcacgcct tttttttt 58

<210> SEQ ID NO 23
<211> LENGTH: 22
<212> TYPE: DNA
<213> ORGANISM: Artificial Sequence
<220> FEATURE:
<223> OTHER INFORMATION: LNA-CS1

<400> SEQUENCE: 23
acactgacga catggttcta ca 22

<210> SEQ ID NO 24
<211> LENGTH: 22
<212> TYPE: DNA
<213> ORGANISM: Artificial Sequence
<220> FEATURE:
<223> OTHER INFORMATION: LNA-CS2

<400> SEQUENCE: 24
tacggtagca gagacttggt ct 22

<210> SEQ ID NO 25
<211> LENGTH: 22
<212> TYPE: DNA
<213> ORGANISM: Artificial Sequence
<220> FEATURE:
<223> OTHER INFORMATION: LNA-CS2rc

<400> SEQUENCE: 25
agaccaagtc tctgctaccg ta 22

<210> SEQ ID NO 26
<211> LENGTH: 11
<212> TYPE: DNA
<213> ORGANISM: Artificial Sequence
<220> FEATURE:
<223> OTHER INFORMATION: forward primer region sequence

<400> SEQUENCE: 26
cgtcgaggcc c 11

<210> SEQ ID NO 27
<211> LENGTH: 15
<212> TYPE: DNA
<213> ORGANISM: Artificial Sequence
<220> FEATURE:
<223> OTHER INFORMATION: thrombin binding aptamer (TBA)

<400> SEQUENCE: 27
ggttggtgtg gttgg 15

<210> SEQ ID NO 28
<211> LENGTH: 53
<212> TYPE: DNA
<213> ORGANISM: Artificial Sequence
<220> FEATURE:
<223> OTHER INFORMATION: control DNA

<400> SEQUENCE: 28
atcgggtgtg ggtggcgtaa agggagcatc ggacaaaaaa aaagccaccc aaa 53

DNA-ENCODED FUNCTIONALIZED APTAMERS

CROSS-REFERENCE TO A RELATED APPLICATION

The present application is a U.S. National Phase of International Application No. PCT/CA2021/050899, filed on Jun. 30, 2021, and claims priority from U.S. provisional patent application Ser. No. 63/045,938 filed on Jun. 30, 2020, the content of which are herewith incorporated in their entirety.

TECHNICAL FIELD

It is provided the synthesis of an aptamer-like encoded oligomer and a library of same.

BACKGROUND

Aptamers are oligonucleotide sequences that specifically bind relevant targets due to their well-defined sequence-dependent tertiary structures. Aptamers are attractive alternatives to antibodies because of their stability and smaller-size, and are more versatile than small molecules due to their specific 3D shape. Complex targets that are considered "undruggable" with small molecules such as protein-protein interactions (PPIs) can be efficiently targeted.

As oligonucleotides, they are easy to synthesize through solid-phase synthesis (SPS), are less immunogenic than antibodies, and potent sequences can be obtained from large libraries through in vitro selection, also known as systematic evolution of ligands by exponential enrichment (SELEX). However, the chemical space offered by aptamers (4 nucleobases: ATGC or AUGC) is much narrower than proteins (20 amino acids with very different functional groups). This has made the discovery of high affinity-binding sequences with no off-target binding difficult in many cases. In addition, due to their nucleic acid nature, aptamers are susceptible to nuclease degradation leading to short half-lives in vivo, and they suffer from poor cellular uptake and renal clearance. These major drawbacks have considerably slowed the emergence of therapeutic applications, and currently only one aptamer drug (pegaptanib, Macugen®) has been approved by the United States Food and Drug Administration (FDA).

To improve the properties of oligonucleotide aptamers, many scientists have chemically modified DNA and RNA nucleobases. Five recent strategies highlight significant steps forward in the field: (i) Slow off-rate modified aptamers (SOMAmers) consisting of introducing nucleotides bearing amino acid-like side-chains (Gold et al., 2010, PLoS One, 5(12): e15004); (ii) click-SELEX allows the addition of an unnatural modifier to an alkyne containing base during SELEX (Pfeiffer et al., 2018, Nat. Protoc., 13(5): 1153-1180); (iii) ligation of modified short nucleic acids fragments on an evolved template (Hili et al., 2013, J. Am. Chem. Soc., 135(1): 98-101); (iv) AEGIS-SELEX (artificial expanded genetic information systems) allowed for the incorporation of artificial base pairs Z and P with modified hydrogen bonding motifs orthogonal to those present in the canonical bases of DNA and RNA (Sefah, K.; Yang, Z.; Bradley, K. M.; Hoshika, S.; Jiménez, E.; Zhang, L.; Zhu, G.; Shanker, S.; Yu, F.; Turek, D., In vitro selection with artificial expanded genetic information systems. *Proceedings of the National Academy of Sciences* 2014, 111 (4), 1449-1454.); and (v) polymerases and reverse-transcriptases capable of reading and synthesizing backbone-modified oligonucleotides (xeno-nucleic acids, XNA) were developed (Loakes et al., 2009, Chem. Commun., 31: 4619-4631).

The three first methods offer the possibility to modify only few nucleotides of a given strand and the last two yielded few aptamers so far. These strategies also all rely on nucleotides with relatively conservative modifications to natural nucleic acids to allow for enzyme-aided amplification or ligation.

There is still a need to be provided with a mean to incorporate a modular number of non-nucleosidic functional modifications to aptamers.

SUMMARY

It is provided a method of preparing aptamer-like encoded oligomer (ALEnOmer), said method attaching a branching unit at the 5' end of a first DNA branch attached to a solid support for generating a second branch linked to the first branch by the branching unit; extending in parallel the first branch by coupling at least one nucleotide with an orthogonal protecting group and the second branch by coupling at least one phosphoramidite monomer with an orthogonal protecting group, wherein the extension of the second branch producing an oligomer; separating the solid support into a number of aliquots of solid supports; incorporating at least one phosphoramidite building block on the second branch and at least one DNA codon of the second branch building block at the 5' end of the first branch; pooling the aliquots of solid supports together; g) cleaving the ALEnOmer from the solid support and deprotecting the ALEnOmer; and h) isolating and purifying the full-length ALEnOmer.

In an embodiment, the method provided herewith comprises a first step of synthesizing the first DNA branch by solid phase synthesis.

In an embodiment, a linker is added to the second branch.

in an embodiment, the linker comprises a fluorescent label.

In another embodiment, the at least one monomer protecting group is dimethoxytrityl (DMT), monomethoxytrityl (MMT), or levulinyl.

In a further embodiment, the at least one nucleotide orthogonal protecting group is dimethoxytrityl (DMT), monomethoxytrityl (MMT), or levulinyl.

In another embodiment, the levulinyl is orthogonally deprotected using hydrazine prior to being branched.

In an embodiment, a different phosphoramidite building block is incorporated in each aliquots of solid supports.

In an embodiment, the first branch and second branch are extended by coupling a 5' dimethoxytrityl (5'-DMT) followed by coupling a 5'-levulinyl phosphoramidite.

In another embodiment, the branching unit is attached after the 20$^{th}$ nucleotide at the 5' end of the first branch.

In a further embodiment, the first branch comprises from the 5' to 3' ends a primer region, the codons associated to the oligomer sequence, and a reverse-primer region.

In another embodiment, a spacer is added to the first branch.

In a further embodiment, the spacer is a fluorescent label.

In an additional embodiment, the oligomer has a degree of polymerization of at least 5, preferably of at least 8.

In another embodiment, the oligomer has a degree of polymerization of >15.

In a further embodiment, the at least one nucleotide orthogonal protecting group is incorporated on the second branch and the at least one monomer phosphoramidite orthogonal protecting group on the first branch.

In an embodiment, the oligomer is an aptamer.

In another embodiment, the aptamer comprises at least one unnatural monomer.

In a particular embodiment, the unnatural monomer is at least one of a phosphoramidite monomer Alk, an anthracene modification (Ant), a phosphoramidite monomer Bal, a phosphoramidite monomer C12, an histidine-like modification (His), a phenylalanine modification (Phe), a Naphthalene (Nap), a carbohydrate-containing modification (Sug), and a tryptophan-like modification (Trp).

In a further embodiment, the solid support is a Pore Glass (CPG) solid support.

In another embodiment, method steps are repeated producing a library of ALEnOmers.

It is also provided an aptamer-like encoded oligomer (ALEnOmer) comprising a DNA coding strand covalently attached to an oligomer through a branching unit, wherein the oligomer has a degree of polymerization of at least 5 and is an aptamer.

In an embodiment, the oligomer has a degree of polymerization of >15.

In a further embodiment, the ALEnOmer is produced by the method provided herein.

It is also provided a branching unit molecule comprising the structure of formula (I);

(I)

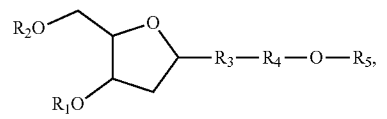

wherein $R_1$ is a phosphoramidityl residue consisting of:

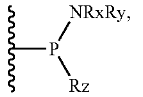

wherein Rx and Ry are selected from the group consisting of $C_{1-10}$ branched alkyl, $C_{1-12}$ alkyl, and cyclic hydrocarbyls; and Rz is a phosphite-protecting group;

$R_2$ and $R_5$ are dimethoxytrityl (DMT), monomethoxytrityl (MMT) or a Levulinyl protecting group;

$R_3$ is uracil, thymine, guanine or adenine; and $R_4$ is a spacer.

In an embodiment, $R_4$ is a spacer from 2 to 20 atoms long.

In a further embodiment, $R_4$ contains carbon, oxygen, or nitrogen.

In a supplemental embodiment, the branching unit is:

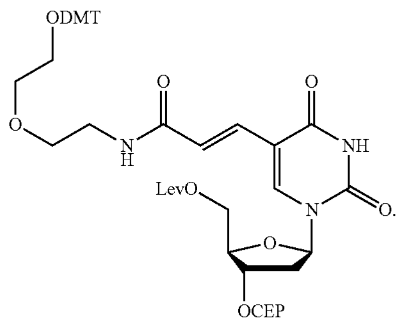

It is further provided a DNA-encoded library (DEL) comprising a mixture of aptamer-like encoded oligomers (ALEnOmers) comprising a DNA coding strand covalently attached to an oligomer through a branching unit, wherein the oligomers have a degree of polymerization of at least 5, preferably at least 8, alternatively of at least 15.

BRIEF DESCRIPTION OF THE DRAWINGS

Reference will now be made to the accompanying drawings.

DETAILED DESCRIPTION

Figure 1:
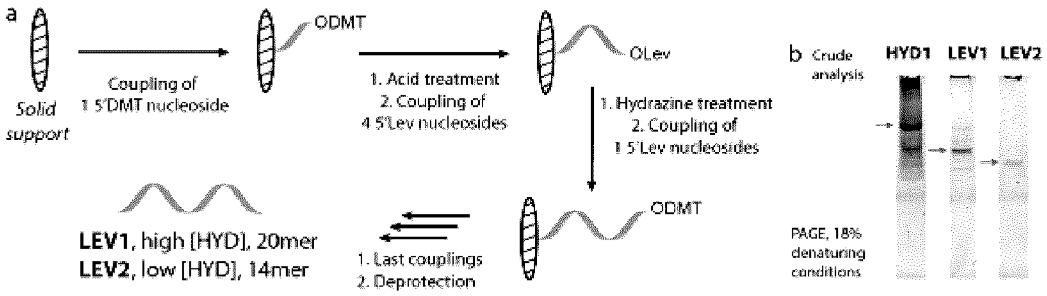
FIG. 1 illustrates the synthesis of DNA strands with 5'-Lev and 5'-DMT phosphoramidites, showing in (a) the synthesis of LEV1 and LEV2 and in (b) the crude mixture analysis of HYD1 (45mer, 30 hydrazine (0.5 M) treatments, no 5'-Lev amidites, acetyl protected cytidines), LEV1 (20mer, 15 hydrazine (1.5 M) treatments, 15 5'-Lev amidites, benzoyl-protected cytidines), LEV2 (14mer, 10 hydrazine (0.5 M) treatments, 10 5'-Lev amidites, benzoyl-protected cytidines).

In accordance with the present disclosure, there is provided an aptamer-like encoded oligomer (ALEnOmer), method of producing same and method of preparing a library of ALEnOmes.

The synthesis of a novel type of DNA-encoded library is described. DNA-encoded libraries let drug companies screen trillions of potential ligands in a single, simple experiment. DNA-encoded libraries have become a mainstay of drug discovery within the past 5 years. To-date, DNA-encoded ligands have been limited to small molecules, peptides, proteins, or short oligomers. It is provided herein a mean to expand the scope of ligands to long oligomers (degree of polymerization >15).

Sequence-defined oligomers made of unnatural building blocks can be used as biologically relevant ligands with improved properties compared to their natural counterparts such as oligonucleotide aptamers. The term "unnatural" as used herein in means that the chemical structure is unrelated to those found in biological systems. Accordingly, the term "unnatural monomer" as used herein refers to monomers which core structure is unrelated to those of monomers found in biological systems. Herein, it is provided the synthesis of DNA-encoded sequence-defined functionalized aptamers that will enable the selection and identification of potent target binding sequences from a large highly functionalized library. The use of levulinyl protecting groups is shown to be fully orthogonal to dimethoxytrityl and allows the parallel synthesis of two oligo(phosphodiester)s. Therefore, on a solid phase support, a DNA code made of nucleotide phosphoramidites was synthesized simultaneously with a sequence-defined oligomer made of non-nucleosidic monomers. Using the split-and-pool combinatorial strategy, a library of ~300,000 DNA-encoded unnatural aptamers based on the thrombin-binding aptamer sequence was synthesized. Monomers used were designed to improve affinity to thrombin, increase the aptamer serum half-life, and potentially help cellular transfection. The oligonucleotide of a control DNA-encoded structure was amplified and sequenced successfully from very low concentrations to show the possibility to use the library for target affinity selection. Binding affinity measurements of three model DNA-encoded aptamers was performed and confirmed the relevance of the library design.

These DNA-oligomer libraries present a unique opportunity to identify new aptamers. Aptamers are a class of oligonucleotide molecules that can specifically bind proteins or small molecules, and they hold great potential for both diagnostic and therapeutic applications. Compared to antibodies, aptamers are straightforward to synthesize through solid-phase synthesis (SPS) in high yield, have improved thermal stability, no batch-to-batch variation, and a long shelf life. Compared to small molecules, aptamers are less likely to have off-target effects and can be used to modulate complex systems such as protein-protein interactions. However, existing aptamers are composed of conventional or moderately-modified nucleotides, which is a restricted chemical space. The aptamers provided herein are composed of numerous structurally diverse non-nucleosidic modifications (e.g. containing alkyl chains, amino acids, carbohydrates, aromatic moieties, alkyne) alongside conventional nucleotides. The non-nucleosidic modifications should improve the binding affinity of the aptamers to the target of interest, increase resistance to nucleases, and improve cellular uptake.

The DNA-encoded library consists of a DNA strand "tag" covalently attached to a highly functionalized oligomeric ligand. In an embodiment, the ligand is an oligo(phosphodiester) composed of versatile artificial phosphoramidite monomers. The sequence of nucleotides in the DNA tag codes for the specific chemical composition of the oligomeric ligand. Contrary to most DNA-encoded libraries, both the long oligomers and the DNA tag can be produced by solid-phase automated synthesis, combined with highly efficient phosphoramidite chemistry and two orthogonal protecting groups (dimethoxytrityl and levulinyl). In contrast, DNA-encoded libraries are made by sequential organic reactions (usually compatible with organic solvents) and DNA ligation (in water).

Accordingly, it is provided a method of preparing aptamer-like encoded oligomer (ALEnOmer), the method comprising synthesizing a DNA strand by solid phase synthesis consisting of a first branch with a 3' end attached to a solid support and a 5' end; attaching a branching unit at the 5' end of the first branch for generating a second branch linked to the first branch by the branching unit; extending in parallel the first branch by coupling at least one nucleotide with an orthogonal protecting group and the second branch by coupling at least one phosphoramidite monomer with an orthogonal protecting group, wherein the extension of the second branch producing an oligomer; separating the solid support into a number of aliquots of solid supports; incorporating at least one phosphoramidite building block on the second branch and at least one DNA codon of the second branch building block at the 5' end of the first branch; pooling the aliquots of solid supports together; cleaving the ALEnOmer from the solid support and deprotecting the ALEnOmer; and isolating and purifying the full-length ALEnOmer. The ALEnOmer produced comprises a DNA coding strand covalently attached to an oligomer through a branching unit, wherein the oligomer has a degree of polymerization of at least 5, preferably of at least 8, and is an aptamer. The library is prepared by repeating these steps.

As a proof of concept, a library of ~300,000 DNA-encoded non-nucleosidic aptamer ligands were synthesized.

The library scaffold is designed based on an existing conventional oligonucleotide aptamer that binds to thrombin. The oligonucleotide of a control DNA-encoded structure was PCR amplified and sequenced successfully from very low amounts ($10^{-20}$ moles) to demonstrate the potential to use the library. Model DNA-encoded non-nucleosidic oligomers bound to thrombin with good affinity, demonstrating the potential to find non-nucleosidic oligomer ligands in the library that display higher binding affinity to thrombin compared to the conventional aptamer.

The use of oligomers instead of small molecules for ligand discovery is very attractive as epitomized by the rise of antibodies and aptamer-based ligands approved as drugs and as diagnosis tools. The longer size of oligomers is necessary to identify more specific ligands, with better biological activity and limited off-target effects. The use of oligomers rather than small molecules further enables the ability to target more complex systems; such as the ability to modulate protein-protein interactions which are considered as “undruggable” with small molecules.

Aptamers are superior to antibodies in several aspects: they are less-immunogenic, less sensitive to variations in temperature and most importantly, they are made through chemical synthesis. However, aptamers have the drawback of being made of only 4 different building blocks (4 nucleotides, A, T, C and G).

Contrary to known technologies which involve an enzyme-based recognition, ligation or polymerization step that prevents the use of building blocks that are significantly different to nucleotides, the present technology allows any kind of building block as long as it is suitable for phosphoramidite chemistry-based SPS. As such, the method provided herein increases the availability of building blocks that can be used, which subsequently expands the chemical landscape of ligands that can be screened in an exponential manner. The synthetic method provided herein for generating DNA-encoded non-nucleosidic ligands libraries presents the advantage to be very modular under several aspects: (i) the same library can be used for several targets; (ii) the proof of concept involves natural nucleotides and 9 artificial building blocks but many other commercially available DNA modification reagents as well as modified DNA bases can be used and are encompassed herein; and (iii) the size of the library can be modified.

Finally, the anionic nature of the oligomers described herein permits reliable purification of pure product through gel electrophoresis, reducing the selection of false positives related to truncated products. This purification step before selection cannot be performed with existing DNA-encoded libraries.

The phosphoramidite chemistry is used herein for the aptamer on the branch as well as the code. Therefore, an orthogonal protecting group to the common dimethoxytrityl (DMT) is required. This new group must fulfil several criteria: (i) it needs to be resistant to all reagents used in a DNA synthesizer, (ii) it must be quickly and quantitatively removed and (iii) classical DNA protecting groups on nucleotides and phosphates need to stay unaltered to the orthogonal deprotection conditions. A silylated protecting groups were firstly used. For example, tert-butyldimethylsilane (TBDMS) and triisopropylsilyloxymethyl (TOM) 2'-hydroxyl protection of RNA are resistant to synthesizer reagents. However, it was not possible to determine an efficient and orthogonal way to deprotect the TBDMS and TOM groups. Accordingly, silylated protecting groups lead to unsuccessful attempts due to the incompatibility of the deprotection process with the unnatural monomers. 2'-acetoxy ethyl orthoester (ACE) RNA chemistry involves the use of a silylated group at the 5' end of RNA nucleotides that is readily deprotected using hydrofluoric acid (HF) in triethylamine (TEA). However, this imposes the use of a methyl group instead of a cyanoethyl as phosphate protection, requiring harsher deprotection conditions that may not be compatible with the unnatural monomers of the aptamers. The use of the trimethylsilylethoxycarbonyloxy (Teoc) protecting group was also explored. A 5'-Teoc protected thymidine nucleoside was made and successful attachment to a DNA 19mer was achieved. The Teoc group showed resistance to synthesizer reagents and was orthogonally deprotected using tetrabutylammonium fluoride (TBAF) for 10 minutes. However, several TBAF treatments during a common DNA strand synthesis did not lead to satisfactory yields. TBAF probably deprotects cyanoethyl groups and alters Controlled Pore Glass (CPG) solid support. Polystyrene beads as an alternative to CPG are not recommended for long and branched oligomers similar to the ones we want to make.

The levulinyl group (Lev) can be used as a protecting group in oligonucleotide synthesis. It can be orthogonally deprotected using hydrazine to make branched oligonucleotides. It was examined whether the levulinyl group could be used efficiently multiple times to grow two different strands simultaneously from a branching point using the same CPG. HYD1 is a 47mer DNA strand synthesized according to standard DNA synthesis protocols, except that a hydrazine solution was injected 30 times during the synthesis. Yields were satisfactory but the synthesis led to a crude mixture containing multiple byproducts as observed by polyacrylamide gel electrophoresis (PAGE). It is believed the main reason for the presence of byproducts was the use of acetyl protected cytidine phosphoramidite, which can be deprotected during hydrazine treatment. Therefore the next tests were performed with benzoyl-protected cytidine. Conveniently, 5'-levulinyl deoxynucleotide monomers are commercially available. Two DNA strands were synthesized: a 20mer and 14mer termed LEV1 and LEV2 respectively, by coupling 5' DMT-phosphoramidites followed by 4 5'-levulinyl phosphoramidite couplings. Steps involving trityl response allowed to visually assess the coupling efficiency during the synthesis. Both LEV1 and LEV2 were synthesized in high yields. Gel electrophoresis revealed that the synthesis was cleaner than HYD1 further demonstrating that acetyl protected cytidine was the main issue encountered during initial tests. 5'-levulinyl monomers of LEV2 were deprotected using 0.5 M hydrazine solution as reported (Katolik et al., 2014, J, Org. Chem., 79(3): 963-975) while higher concentrations of hydrazine were used for LEV1. Mass spectrometry (MS) and gel electrophoresis analyses revealed that the crude mixture of LEV1 contained species with higher masses than the expected product. It was hypothesized that base deprotection may still happen during the synthesis leading to the formation of branched byproducts. On the contrary, no byproduct was identified in the analysis of LEV2. Further optimization showed that deprotection time could be lowered from 32 to 6 minutes. These results confirmed that the levulinates are good orthogonal protecting groups for the parallel synthesis of branched oligonucleotides on solid phase.

Figure 2:
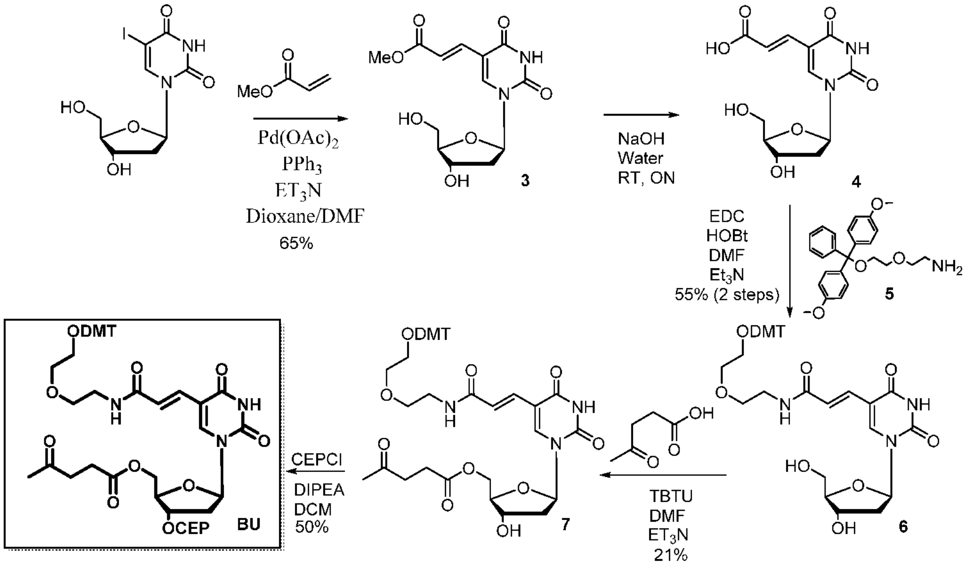
FIG. 2 illustrates the synthesis of branching unit BU, wherein CEP=cyanoethylphosphoramidite.

DMT-protected monomers were used for the aptamer branch. This choice was motivated by the possibility to visually gauge the more challenging unnatural monomer couplings efficiency thanks to the DMT cation orange color. The other part would be 5'-levulinyl protected for growing the code. For the branch point, a deoxyuridine modified was designed with an acrylamido side chain at the C5 position (see FIG. 1). This modification still allows efficient DNA hybridization and can even be bypassed by some polymerases efficiently. Starting with the Mizoroki-Heck coupling of iodouridine with methyl acrylate, the ester obtained was deprotected and underwent an amine coupling with DMT protected 2-(2-amino)ethoxyethan-1-ol. The protection of the 5'-OH of 3 with a levulinyl group was then performed to yield compound 7 which was finally turned into phosphoramidite BU (see FIG. 2).

Figure 3:
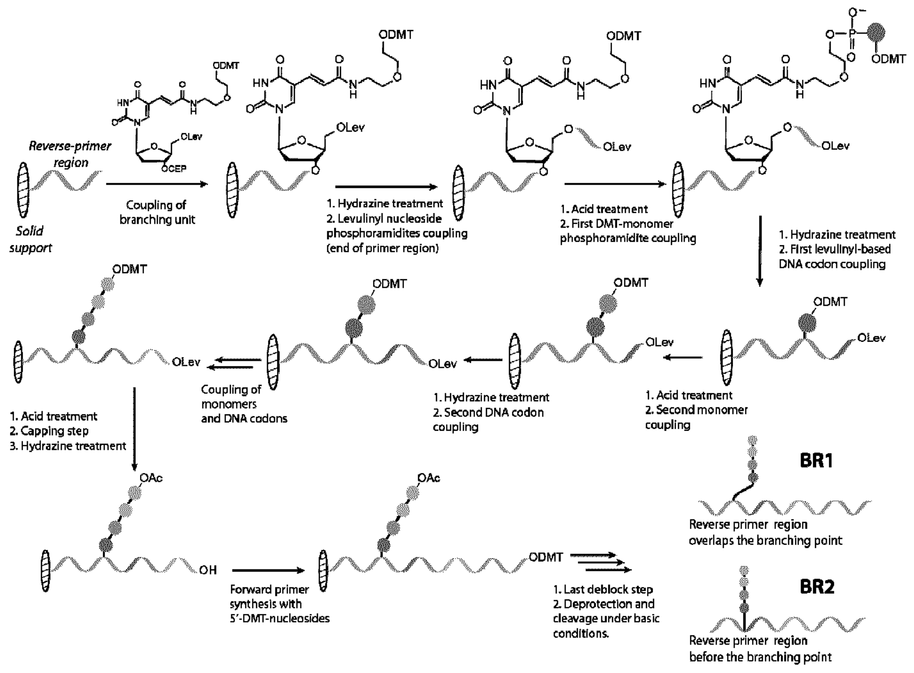
FIG. 3 illustrates the parallel synthesis of branched oligo (phosphodiester)s.

Synthesis of two model branched strands, BR1 and BR2 was first examined by exclusively using DNA nucleotides (see FIG. 3). BR1 is designed so that the reverse primer would bind over the branching unit, while for BR2, the whole reverse primer would hybridize at the 3' end of the branching unit. The "aptamer branch" for these strands is a DNA 4mer. It is recommended the attachment of the branching unit on a growing chain on CPG after the $20^{th}$ nucleotide to prevent steric hindrance close to the solid support. Therefore, BR1 synthesis started with a 9-thymidine linker followed by 12 nucleotides forming the main part of the reverse primer region of BR1. BU was then incorporated efficiently. Four nucleotides belonging to the reverse primer region of the code were added at the 5' end of BU using 5'-levulinyl chemistry. On the branch, the aptamer was synthesized with 5'-DMT phosphoramidites. After each 5'-DMT monomer insertion, DMT was kept on while a codon was synthesized on the code branch. 2-nucleotide codons were used at this point as a proof of concept. This resulted with a DNA 4mer as the aptamer and a DNA 8mer as the code. The last aptamer nucleotide was deprotected and intentionally capped with usual capping reagents.

In a particular embodiment and as exemplified herein, the branching unit molecule encompassed herein comprises the structure of formula (I);

(I)

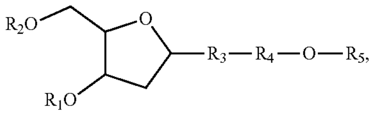

wherein $R_1$ is a phosphoramidityl residue consisting of:

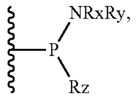

wherein Rx and Ry are selected from the group consisting of $C_{1-10}$ branched alkyl, $C_{1-12}$ alkyl, and cyclic hydrocarbyls; and Rz is a phosphite-protecting group;

$R_2$ and $R_5$ are dimethoxytrityl (DMT), monomethoxytrityl (MMT) or a Levulinyl protecting group;

$R_3$ is uracil, thymine, guanine or adenine, connected to the sugar backbone the same way than in a nucleotide; and $R_4$ is a spacer, that can be from 2 to 20 atoms long and can contain carbon, oxygen, nitrogen.

It is encompassed that DMT/MMT and Lev are interchangeable. Preferably, DMT is inserted at $R_5$ and Lev as $R_2$.

In an embodiment, the encompassed branching unit is:

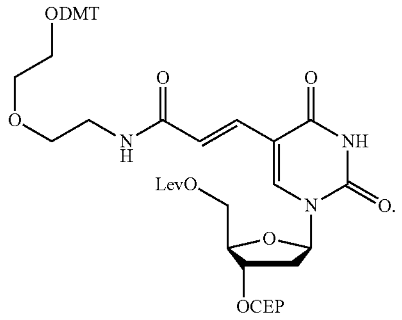

Initial tests have shown the resistance of acetyl ester to hydrazine treatment. Indeed, during a regular 19mer synthesis, the 5' end was capped and underwent multiple hydrazine treatments. Further couplings failed while trityl response was optimal in the case of an uncapped control. Therefore, the 5' end of the code could be deprotected with hydrazine and elongated with the forward primer region (11 nucleotides) using DMT chemistry. In view of the trityl response, it was possible to visually observe if the code synthesis had been efficient. BR2 synthesis started with the entire 17-mer primer region, followed by BU and similar aptamer and code than BR1. Yields were low (~5%) according to gel electrophoresis image analysis but high enough to isolate BR1 and BR2. After gel purification, the formation of the expected branched oligonucleotide was confirmed by liquid chromatography coupled to mass spectrometry.

Figure 4:
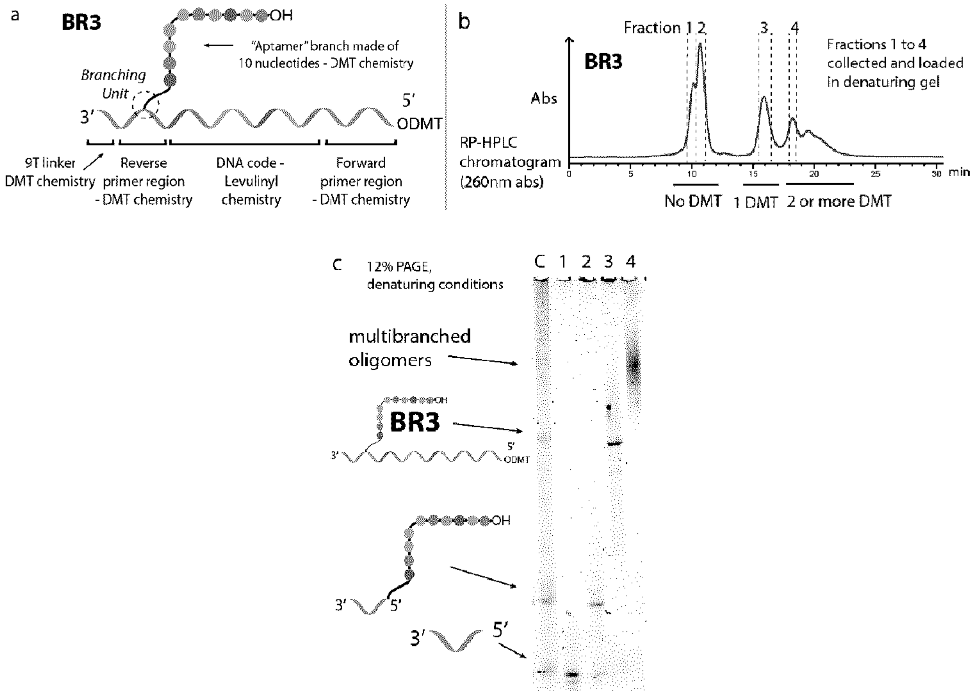
FIG. 4 illustrates the BR3 synthesis, showing in (a) a schematic representation of BR3; in (b) RP-HPLC of crude mixture obtained from synthesis of BR3 with DMT-on; and in (c) gel analysis of crude mixture (lane C) and HPLC fractions (lanes 1 to 4), wherein coupled to MS results, this in-depth analysis revealed the nature of the synthesis' main by products.

A new design BR3 was synthesized to further show the applicability of the provided strategy to longer strands. BR3 is similar to BR1 except that the aptamer branch contains 10 nucleotides instead of 4 and the code is made with 10×2=20 nucleotides instead of 8. Again, the aptamer branch was capped at the end of its synthesis and continued the code with 5'-DMT phosphoramidites for the forward primer region synthesis. The DMT was left on at the 5' end of the code branch to get an insight into the byproducts formed. After deprotection from the solid support, the crude product was analyzed by reverse-phase high-performance liquid chromatography (RP-HPLC), gel electrophoresis and mass spectrometry (FIG. 4). The expected product was obtained in yields between 10 (determined by gel electrophoresis image analysis) and 22% (determined by HPLC chromatogram analysis). While this number can be further improved, it allowed the isolation of BR3 through gel purification. The DMT-on strategy revealed that most byproducts do not have the full DNA code on. In other words, they are the result of failed couplings on the code part. Through MS, the DNA strand before BU coupling was identified and the strand comprising the aptamer and the 3' DNA section but missing the code. Thus, the branching unit coupling as well as the first levulinyl phosphoramidite coupling are low yielding. Longer coupling and deprotection times for these phosphoramidites were therefore implemented. Some species with longer retention times than the expected DMT-on product were also observed. Mass spectrometry and gel electrophoresis revealed higher masses and lower mobility than BR3 (FIG. 4*c*) indicating that byproducts of larger size and probably containing another or several other DMT groups are present. Similarly to LEV1, hydrazine deprotects small amounts of DNA bases leading to the formation of minor oligomeric byproducts with several branches.

Accordingly, the successful synthesis of BR1, BR2 and BR3 demonstrates that the provided strategy to grow two different strands simultaneously is successful. From BU, the aptamer and the code could be synthesized in parallel.

Contrary to aptamers developed through SELEX and other modified aptamer synthesis, non-nucleosidic modifications were used. These non-nucleosidic modifications prevent amplification using enzymatic reactions. As such, the selection step would need to be followed by DNA-code amplification and sequencing. At this point, binding sequences can be synthesized efficiently without the code through automated SPS and tested. If desired, another round of selection could then be set up. Indeed, sequences of interest can be "evolved" manually or using an appropriate software and a new library synthesized through automated SPS for the next selection round.

Thrombin is a protein involved in coagulation mechanisms. The thrombin binding aptamer (TBA) with sequence 5'-GG-TT-GG-TGT-GG-TT-GG-3' (TBA; SEQ ID NO: 27) is a G-quadruplex-forming 15mer. It is demonstrated herein the possibility of trying very large numbers of aptamers with several modifications at once. A modified aptamer was exemplified so that the G-tetrads stay intact while the loops would be modified with one or two monomers from the new library. All modifications of the loop are expected to influence the global G quadruplex stability. The TT loops are in close proximity to thrombin in TBA-thrombin complexes, hence modifications in these regions should greatly influence the binding affinity to thrombin. The 3' end of the aptamer was also modified since some reports showed a potential increase in stability at this position.

Figure 5:
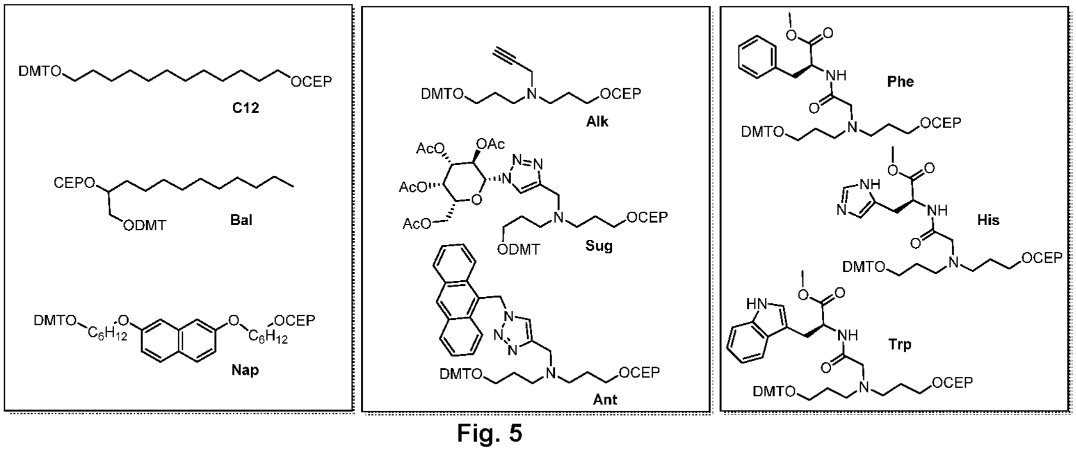
FIG. 5 illustrates phosphoramidite monomers used in an embodiment, wherein CEP=Cyanoethylphosphoramidite, DMT=dimethoxytrityl.
Figure 6:
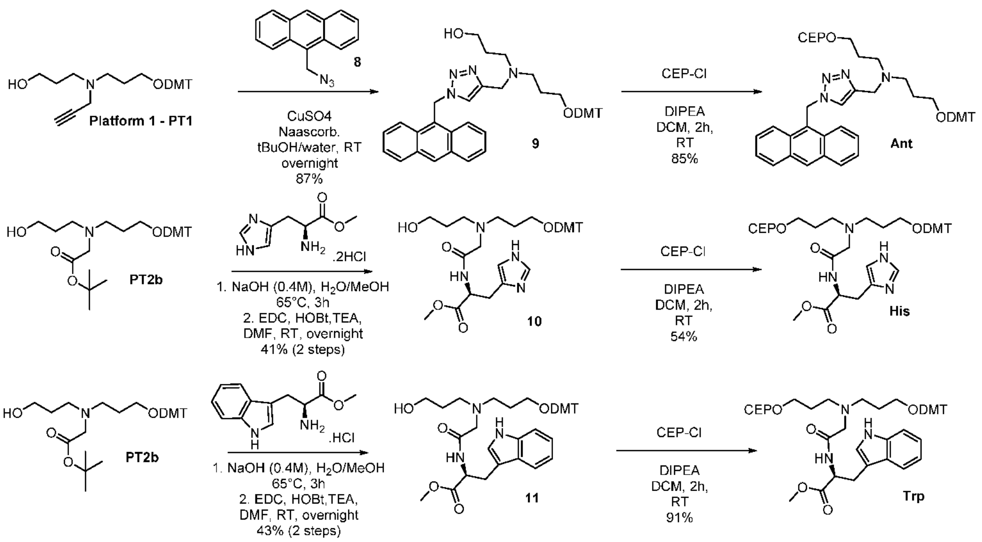
FIG. 6 illustrates the synthesis of Ant, His, Trp in accordance to an embodiment.

The monomers shown in FIG. 5 were selected. C12 was chosen to improve hydrophobic interactions with thrombin. Naphthalene (Nap) has been shown to improve aptamer binding affinity to some targets. Therefore, Nap represented a good candidate for π-π stacking and hydrophobic interactions. Thanks to the versatility of the method provided herein, modifications can be designed and synthesized at will following criteria dictated by the protein being studied. Moreover, the positive charge on the tertiary nitrogen at physiological pH could improve cellular uptake properties of our constructs, which is appealing for targeted therapy applications (aptamer-drug conjugates). It is exemplified herein reported the phenylalanine modification (Phe), the synthesis of a histidine-like (His) and a tryptophan-like (Trp) modification (as seen in FIG. 6). These aromatic ring-containing modifications could create π-π stacking, polar and hydrogen-bonding interactions with thrombin. Alk was also used as a small moiety with a positive charge that can be turned into a functional group through click chemistry after SPS. Finally, the carbohydrate-containing (Sug) and anthracene (Ant) modifications were used to expand the structural diversity of aptamer modifications. His, Trp and Ant syntheses further demonstrate the versatility of the synthetic method described herein (FIG. 6).

Figure 7:
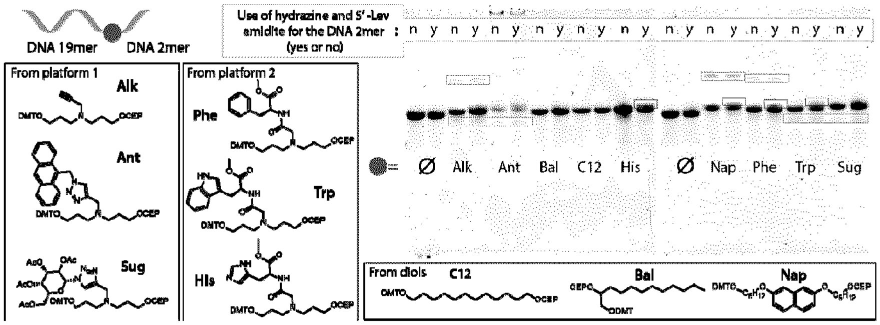
FIG. 7 illustrates the synthesis of modified DNA 21mers and analysis of hydrazine influence, herein crude mixture post-SPS and deprotection were analyzed through 15% PAGE in denaturing conditions, wherein for each modification, lanes with a 'y' show strands tested with hydrazine and 5'-Lev amidite while lanes with a 'n' were made following a standard protocol.

It is provided the high yielding incorporation of the 9 unnatural monomers (Alk, Ant, Bal, C12, His, Phe, Nap, Sug, Trp as can be seen in FIG. 5) at internal positions of a DNA strand and their compatibility with hydrazine through the following experiment (FIG. 7). The 9 phosphoramidites were coupled to model DNA 19mers on solid support. After the capping and oxidation steps, the solid support was divided into two aliquots. The first one underwent 10 hydrazine treatments before deblocking the 5'-DMT protecting group. Then, the coupling of a 5'-Levulinyl followed by 10 other hydrazine treatments and a 5'-DMT phosphoramidite coupling were performed. The DNA strands on the CPG of the second aliquot underwent similar reactions except that no hydrazine treatment nor 5'-Lev phosphoramidites were involved. An unmodified strand was also synthesized using the same conditions. Crude mixtures were analyzed by gel electrophoresis (FIG. 7). Very small amounts (<10%) of potential dimers visible in lanes Alk, Nap and Phe and of unmodified DNA 19mer visible in lanes Alk, Ant, Trp and Sug were found proving the high coupling efficiency of each phosphoramidite. For hydrazine-treated strands, lanes Nap, Phe and Try show a light band on top of the expected product band which may be due to unwanted branched oligomers. The amount of such byproducts is negligible under the specific conditions tested, meaning our phosphoramidites are adapted to the branched oligomer synthetic conditions.

Figure 8:
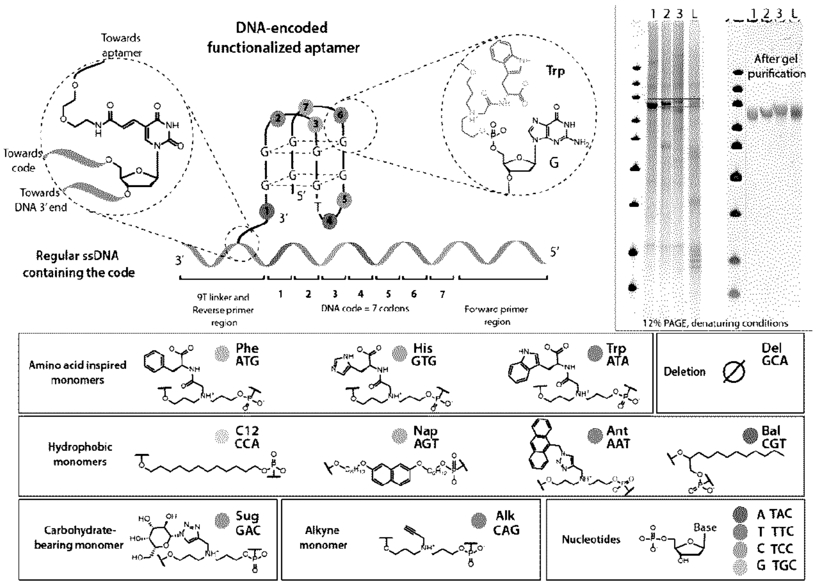
FIG. 8 illustrates the design and synthesis of DNA-encoded thrombin-binding aptamers made of unnatural monomers, wherein lanes 1, 2, 3 and L in the gels were respectively loaded with crude mixtures (left) and purified strands (right) of TBA1, TBA2, TBA3 and LIB; aptamer branch: TBA1, TBA2, TBA3; and LIB is a library of DNA-encoded aptamers with seven positions modified.

Before starting the synthesis of the actual library, three strands of known sequences were made with different numbers of unnatural nucleotides. TBA1 is a strand made of DNA nucleotides only and whose branch is the original TBA, TBA2 has an aptamer branch with three unnatural monomers, one in each loop of the TBA and TBA3 is heavily modified with seven positions bearing a different moiety than on the original TBA sequence (FIG. 8). Synthesis started with a 9-thymidine linker to put the branching unit away from the solid support. 11 nucleotides, part of the 3' reverse primer region, were then attached. The branching unit uridine and the 4 following nucleotides are also part of the reverse primer region on the code. Simultaneously, a 4-thymidine linker is attached on the aptamer branch to prevent interactions between the later formed aptamer and the code. To build the aptamer, a 3-nucleotide codon was first attached to the code followed by the associated monomer on the aptamer. Each GG section on the aptamer is not accompanied with code growth because these are part of the constant regions of the aptamer. In total, seven nucleotides or unnatural monomers were encoded meaning that the aptamer branch was 4 (linker)+7 (unnatural monomers)+8 (GG regions)=20 monomers long while the code was 4 (end of reverse primer region)+21 (7×3 nucleotides coding for the aptamer sequence)=25 nucleotides long. Again, the aptamer branch synthesis was capped allowing the forward primer region to be grown with 5' DMT phosphoramidites. TBA1, TBA2 and TBA3 were synthesized in reasonable yields allowing the isolation of a few nanomoles of each. From gel image analysis, synthetic yields are estimated to be 22% for TBA1, 16% for TBA2 and 10% for TBA3. Mass spectrometry results confirmed the identity of the products. All three strands have similar mobility shifts on gel showing that a library of constructs can be purified by gel electrophoresis techniques. In DNA-encoded libraries, full-length products are usually not separated from the crude mixture. The negatively charged nature of the oligomers described herein allows for easy purification.

Figure 9:
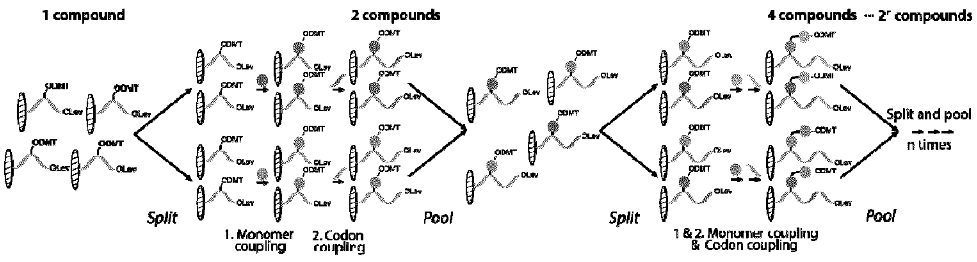
FIG. 9 illustrates the split and pool strategy for the synthesis of a DNA-encoded unnatural aptamer library, showing an example with 2 different monomers at each step for clarity.

After the successful syntheses of TBA1, TBA2, and TBA3, the split-and-pool strategy was applied to make LIB, a library of DNA-encoded aptamers (FIG. 9). When reaching position n of the aptamer, the solid support is split into x aliquots. The determination of equivalent amounts of CPG in each aliquot was performed visually to avoid CPG spilling. This induced a small bias: some sequences may be slightly overrepresented, and others may be underrepresented. 6 different modifications were used at each cycle because it fits the MerMade 6 synthesizer (x=6) used. Each solid support fraction underwent an unnatural monomer or nucleotide coupling on the aptamer branch. This step is followed by the attachment of the associated codon of 3 DNA nucleotides on the code branch. The solid support is then mixed together and split again for the coupling n+1. Attachments of the G bases, which are indispensable to keep the G quadruplex backbone, are executed without split and pool nor DNA codon synthesis. In the end, the library should theoretically be composed of $x^n$ members. It was expected a $6^7$=279,936 members library. The library crude mixture was loaded on a gel for analysis and purification. the presence of a relatively diffuse band corresponding to the mobility of TBA1 to TBA3 strands (FIG. 8) was observed. Gel image analysis allowed to measure yields of synthesis of about 11%. 2.5 nmols of the library was isolated using about $1/6^{th}$ of the crude product obtained (despite the spilling of some CPG during the split-and-pool steps). This amount will allow to perform affinity tests towards thrombin.

a significant difference in amplification and sequencing fidelity. For BR3, TBA1, TBA2 and TBA3, the expected sequence code was found in between 69 and 87% of the reads showing that our templates are suitable for PCR and sequencing. In particular, the error rate obtained using TBA3 is in the same range than the other TBA strands whereas it contained 6 unnatural monomers and was amplified from very low concentrations of templates. The error rates are slightly higher in the code region than in the primer region but values are still in the range of SPS made oligonucleotides.

TABLE 1

Sequencing of amplicons from BR1, BR2, BR3 and TBA1 to TBA3 templates.

| Amplicon | Number of reads | Percentage of expected primer sequence[a] (%) | Average error rate per base for primer sequence[b] (%) | Percentage of expected code sequence (%) | Average error rate per base for code sequence[b] (%) |
|---|---|---|---|---|---|
| BR1 | 28,652 | 94 | 0.53 | 96 | 0.54 |
| BR2 | 34,146 | 95 | 0.49 | 95 | 0.68 |
| BR3 | 36,860 | 94 | 0.35 | 87 | 0.69 |
| TBA1 | 23,325 | 93 | 0.45 | 75 | 1.4 |
| TBA2 | 34,456 | 93 | 0.43 | 69 | 1.7 |
| TBA3 | 58,347 | 93 | 0.41 | 75 | 1.4 |

[a]For BR1 and BR2, the forward primer sequence was searched. For the other strands, the reverse primer sequence was searched.
[b]Approximation obtained from 1-(% expected sequence)^(1/n), n being the length of the sequence examined.

Figure 10:
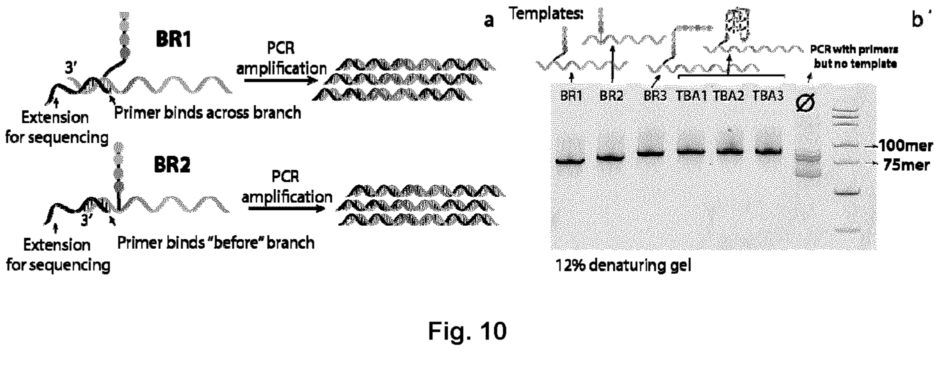
FIG. 10 illustrates PCR with DNA-encoded aptamers as described herein showing in (a) a schematic representation of reverse primer binding BR1 and BR2, wherein primers needed for sequencing have a 22mer tag on both sides; and in (b) amplicons obtained after PCR from the 6 different templates and a control with no template on a denaturing gel.

To show the possible sequencing of strands after selection, PCR amplification of the code of branched oligonucleotides was performed. For PCR, a forward primer was used that has the same sequence as the constant 5' region of the branched oligomers and a reverse primer that hybridizes the 3' region of the strands. BR1 and BR2 were amplified efficiently using a Taq polymerase through hot-start PCR. This demonstrated that the strategies where the reverse primer binds across the branching unit (in BR1) and where it binds before the branch (in BR2) are both suitable (FIG. 10). The strands BR3, TBA1 and TBA2 were shown to amplify efficiently using the same polymerase starting from $\sim 2\times10^{-16}$ moles of template. During the first round of PCR, it was expected the polymerase to produce the complement of the templates code branch from the reverse primers (FIG. 10*a*). From round 2, both template-like sequence and its complementary counterpart should be copied in an exponential way. TBA3 is the strand containing the most unnatural monomers. To show the possibility of amplifying the lowest possible outcome of selected strands from a library of compounds, the amplification of TBA3 code was performed using $\sim 2\cdot10^{-20}$ moles and was shown to be successful (FIG. 10*b*).

The amplicons obtained were indexed and sequenced through MiSeq next-generation sequencing according to standard procedures. Each sequence was read between 20,000 and 60,000 times. The results are summarized in Table 1. For BR1 and BR2, more than 94% of the reads started with the forward primer region sequence. An average error rate per base of ~0.5% was deduced which is standard for SPS-made oligomers. The number of times the correct code sequence was present was also counted and deduced an average error rate between 0.5 and 0.7% for both strands. It shows that, for such templates, having the reverse primer region before or across the branching unit does not lead to The binding affinity of three model compounds containing a fluorescein dye (TBA1F, TBA2F, TBA3F, respectively modified at 0, 2 and 7 positions compared to the original thrombin aptamer) to the target thrombin was tested. The goal of this study was to i) determine if the code strand and branching point impacted binding affinity to the target and ii) compare the affinity of the fully nucleosidic thrombin binding aptamer (TBA1F) to model compounds containing a variety of new non-nucleosidic modifications. Several sequences were included as experimental controls. Specifically, the 15-nucleotide thrombin binding aptamer was included without a code sequence or the branch point (PC). A scrambled sequence, NCS was used as a negative control, as well as the code sequence for TBA1F, synthesized without the aptamer sequence and branch point (NCL).

A fluorescence polarization assay was used to measure the binding affinity of all the model compounds and controls. In this method, excitation light was passed through a polarizing filter causing light to oscillate in a single orientation. Each model compound (TBA1F, TBA2F, TBA3F, NCL, NCS, PC) was modified with fluorescein at the 5' end of the aptamer sequence. Fluorescein absorbed the most energy when it was parallel with the polarization axis of the excitation light. However, during the nanosecond timescale that fluorescein is in the excited state, rotation occurred causing a change in orientation of the emission dipole with respect to the excitation dipole, resulting in size-dependent depolarization of the fluorescein emission signal. In the experiments, when the model compounds specifically bound to the larger thrombin target, the rotational diffusion decreased and a higher polarization of the fluorescent target was observed. However, titration of higher concentrations of the target thrombin resulted in higher depolarization measurements only for model compounds that were specific to thrombin. As such, by plotting the change in depolarization with increasing concentrations of thrombin, binding isotherms were generated for all model compounds studies.

Figure 11:
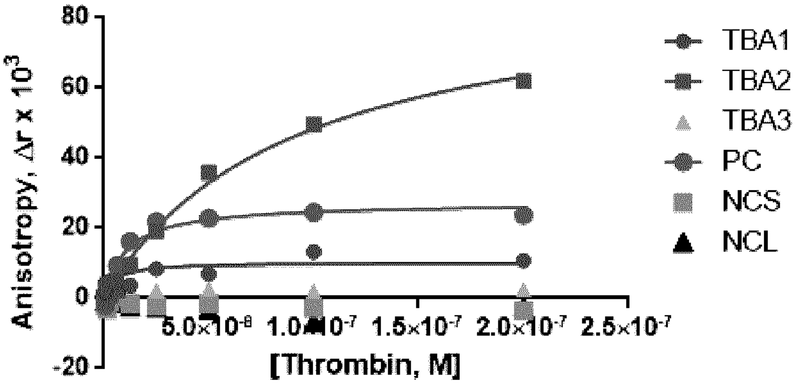
FIG. 11 illustrates a representative binding isotherms generated using fluorescence polarization of model compounds, wherein negative controls (NCS and NCL) and TBA3 showed no change in fluorescence polarization and thus, no binding to thrombin. (•=TBA1, ■=TBA2, ♦=TBA3, ●=PC, ■=NCS, and ▲=NCL).

Binding of the model compounds to the target thrombin was calculated from the binding isotherms as dissociation constants ($K_d$) (see Table 2 and FIG. 11). First, the positive control PC bound to thrombin with an average $K_d$ of 10±2 nM, as expected by the current state of the art. Both negative controls, NCS and NCL, did not result in any binding to thrombin. Interestingly, TBA1F, which is the thrombin aptamer inserted within the branch and code construct, bound to thrombin in the nanomolar range with a $K_d$ of 13±10 nM. The observed decrease in binding is not surprising given that many aptamers lose binding affinity when immobilized or modified at the 5' or 3' end. In this case, the slightly lower binding observed for TBA1F compared to the thrombin aptamer alone (PC) suggests that the ssDNA code stand does not significantly impede binding to the target, and supports the use of the code in a de novo selection or screening experiment as the interference with binding is minimal. Next, TBA2F was determined to bind to thrombin with an average $K_d$ of 89±8 nM. The nanomolar binding indicates that TBA2F is considered a good aptamer and would be sufficient for many applications. Unfortunately, TBA3F did not show any interaction with the target up to 2 μM. It is possible that TBA3F interacts with thrombin at concentrations in the high micromolar range; however, this would not be considered a good aptamer to a protein. These results reflect the low-throughput nature of existing rationale attempts to impart chemical modifications onto existing aptamers. As such, high-throughput screening enabled by the library synthesis is highly desirable. Nevertheless, the high affinity observed for the modified model compound TBA2F shows promise that including non-nucleosidic modifications within the thrombin aptamer yield new high affinity aptamers. Accordingly, it is demonstrated that the branched chain design provided herein can be used to select new potential aptamers containing a broad range of novel non-nucleosidic modifications.

TABLE 2

Binding affinity of model compounds to the target thrombin

| Model compound | $K_d{}^a$ (nM) |
|---|---|
| TBA1F | 13 ± 10 |
| TBA2F | 89 ± 8 |
| TBA3F | NB[b] |
| NCL | NB[b] |
| NCS | NB[b] |
| PC | 10 ± 2 |

[a]All Kd values reported are the mean and standard deviation of at least three independent experiments.
[b]NB = no binding observed with up to 2 μM of thrombin added to the mixture.

It is thus provided a successful synthetic method to generate DNA-encoded unnatural sequence-defined polymers by solid-phase synthesis. This achievement allowed the synthesis of a 300,000 member library of thrombin-binding aptamers with up to 15 monomers. At very low concentrations, the DNA code of an artificial aptamer could be amplified and sequenced, further confirming the validity of our design. As encompassed herein, the monomers described in PCT/CA2019/051091, the content of which is incorporated herewith by reference, greatly enhance the type and number of interactions that these novel aptamers would form with their target. Specifically, model compounds generated showed high affinity binding to a target, thrombin.

Moreover, they are expected to induce better serum stability and cell-internalization properties compared to regular oligonucleotide aptamers.

In the DNA-encoded library (DEL) context, the method provided and disclosed herein is quite different from the synthetic routes reported earlier wherein DNA strand in DEL is synthesized through enzymatic ligation, whereas in the proposed method a solid-phase synthesis is used. Such synthetic route can broaden the chemical space explored by DEL, because it is carried out in non-aqueous solvents and under an inert gas atmosphere. The proposed solid-phase synthesis allows the use of any phosphoramidites commercially available and the use of other non-DNA compatible organic coupling reactions as encompassed herein, in contrast to traditional DEL.

Finally, the present disclosure highlights the potential of combinatorial strategies to help designing potent target-binding sequences with unnatural sequence-defined polymers. The potential of DEL of sequence-defined oligo(phosphodiester)s was demonstrated in the context of potential ligand discovery.

EXAMPLE I

Small Molecule Synthesis, Materials and Instrumentation

All starting materials were obtained from commercial suppliers and used without further purification unless otherwise noted. Acetic acid, Boric acid, solvents were purchased from Fisher Scientific. 4,4'-(chloro(phenyl)methylene) bis(methoxybenzene) (DMT-Cl) and (3-Dimethylaminopropyl)-N'-ethylcarbodiimide hydrochloride (EDC-Cl) were purchased from AK Scientific. O-(Benzotriazol-1-yl)-N,N,N',N'-tetramethylammonium tetra-fluoroborate (TBTU) was purchased from Oakwood Chemicals. Choroform-d1 was purchased from Cambridge Isotope Laboratories. Importantly, it was stored on molecular sieves in order to keep it neutral. If used as sold, hydrolysis of phosphoramidite (fast) as well as DMT deprotection (slow) may be observed. GelRed™ nucleic acid stain was purchased from Biotium Inc. Concentrated ammonium hydroxide, ammonium persulfate, acrylamide/Bis-acrylamide (40% 19:1 solution) and tetramethylethylenediamine (TEMED) were obtained from Bioshop Canada Inc. and used as supplied. 1 μmol Universal 1000 Å LCAA-CPG supports, dry packs, activator solution, 5'-DMT-phosphoramidites used for automated DNA and RNA synthesis were purchased through Bioautomation. Universal 2000 Å LCAA-CPG, N,N-diisopropylamino cyanoethyl phosphonamidic-chloride (CEP-Cl) and 5'-levulinyl phosphoramidites were purchased from Chemgenes. Sephadex G-25 (super fine, DNA grade) and 5'-6-carboxyfluorescein phosphoramidite (6FAM) were purchased from Glen Research. Invitrogen Ultra Low Range ladder was obtained from ThermoFisher Scientific. MyTaq™ HS Red Mix was purchased from Froggabio. QIAquick PCR Purification Kit were obtained from Qiagen. All other reagents were obtained from Sigma-Aldrich, including Thrombin from human plasma. TEAA (triethylammonium acetate) buffer is composed of 50 mM TEA with pH adjusted to 8.0 using glacial acetic acid. TBE buffer is 90 mM Tris, 90 mM boric acid and 1.1 mM EDTA with a pH of 8.0. TAMg buffer is 40 mM Tris, 7.6 mM magnesium chloride and 1.4 mM acetic acid.

Standard automated solid-phase synthesis was performed on a Mermade MM6 synthesizer from Bioautomation. HPLC purification was carried out on an Agilent Infinity 1260. DNA and oligomers quantification measurements were performed by UV absorbance with a NanoDrop Lite spectrophotometer from Thermo Scientific. Eppendorf Mastercycler 96-well thermocycler and Bio-Rad T100™ thermal cycler were used for PCR. PAGE experiments were carried out on a 20×20 cm vertical Hoefer 600 electrophoresis unit and Mini-PROTEAN electrophoresis units. Gel images were captured using a ChemiDoc™ MP System from Bio-Rad Laboratories.

Fluorescence polarization assay was performed on a Synergy™ H4 Hybrid Multi-Mode Microplate Reader from BioTek. Dry solvents were taken from an Innovation Technology device. Low Resolution Mass determination was carried out using Electron-Spray Ionization-Ion Trap-Mass Spectrometry (MS) on a Finnigan LCQ Duo device. High Resolution mass determination was achieved using a Bruker Maxis API (Atmospheric pressure ionization) QTOF or a THERMO Exactive Plus Orbitrap-API. Liquid Chromatography Electrospray Ionization Mass Spectrometry (LC-ESI-MS) of oligomers was carried out using Dionex Ultimate 3000 coupled to a Bruker MaXis Impact™ QTOF. Some oxygen and moisture sensitive experiments were carried out in a Vacuum Atmospheres Co. glove box. Column chromatography was performed using a CombiFlash Rf system from Teledyne Isco. The NMR spectra were recorded on Bruker 400 MHz, 500 MHz, Varian 300 MHz or 400 MHz for $^{1}H$, $^{13}C$ and $^{31}P$ with chloroform-d1 (δ 7.26, $^{1}H$; δ 77.16, $^{13}C$), acetone-$d_6$ (δ 2.04, $^{1}H$; δ 29.8, $^{13}C$) or DMSO-$d_6$ (δ 2.50, $^{1}H$; δ 39.5, $^{13}C$) as internal lock solvents and chemical shift standard.

2-(Trimethylsilyl)ethyl 1H-imidazole-1-carboxylate (1)

1

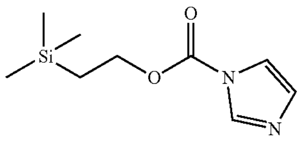

This compound was made following the protocol described in Wincott, F. E., Strategies for oligoribonucleotide synthesis according to the phosphoramidite method. *Current protocols in nucleic acid chemistry* 2000, (1), 3.5. 1-3.5. 12., and 3.78 g of compound 1 was obtained from 2.30 g of 2-(trimethylsilyl)ethan-1-ol. Yields: 91%.

((2R,3S,5R)-3-Hydroxy-5-(5-methyl-2,4-dioxo-3,4-dihydropyrimidin-1(2H)-yl)tetrahydrofuran-2-yl) methyl (2-(trimethylsilyl)ethyl) carbonate (2)

2

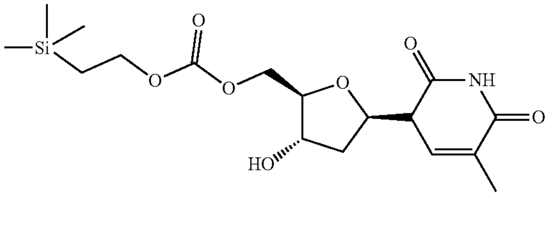

Thymidine (1.52 g, 6.28 mmol, 1 equiv.) and 1,8-Diazabicyclo[5.4.0]undec-7-ene (DBU, 0.19 ml, 1.26 mmol, 0.2 equiv.) were loaded sequentially to a solution of 1 (1.33 g, 6.28 mmol, 1 equiv.) in 0.35 ml of DMF in a dry round bottom flask. The mixture was stirred for 22 h at 25° C. and then cooled in an ice bath as 10 mL of 0.1 N HCl was added.

The aqueous phase was then extracted with ethyl acetate. The combined extracts were dried ($MgSO_4$), filtered, and evaporated. The residue was purified by chromatography on silica gel with slow gradient of DCM/Methanol (0-5%) in about 5 column volumes (CV) to obtain the product as a white solid. 428 mg, 18%.

$^{1}H$ NMR (500 MHz, DMSO-d6): 11.31 (s, 1H), 7.45 (d, J=1 Hz, 1H), 6.18 (t, J=7 Hz, 1H), 5.43 (d, J=4 Hz, 1H), 4.31-4.16 (m, 5H), 3.93-3.90 (m, 2H), 2.19-2.07 (m, 2H), 1.78 (d, J=1 Hz, 3H), 1.01-0.97 (m, 2H), 0.02 (m, 9H).

Methyl (E)-3-(1-((2R,4S,5R)-4-Hydroxy-5-(hydroxymethyl)tetrahydrofuran-2-yl)-2,4-dioxo-1,2,3,4-tetrahydropyrimidin-5-yl)acrylate (3)

3

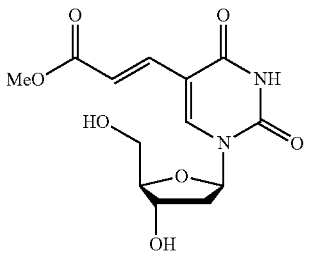

To a solution of 5'-deoxy-5-iodouridine (2.50 g, 7.06 mmol, 1 equiv.), methyl acrylate (1.22 g, 14.1 mmol, 2 equiv.), triphenylphosphine (370 mg, 1.41 mmol, 0.2 equiv.), and triethylamine (1.97 ml, 14.1 mmol, 2 equiv.) in a mixture of dry DMF (25 mL) and dry dioxane (25 ml) was added $Pd(OAc)_2$ (159 mg, 0.706 mmol, 0.1 equiv.) at 25° C. under Ar current. The mixture was heated to 90° C. and stirred for 16 h. The reaction mixture was evaporated under reduced pressure to remove the dioxane followed by coevaporation with toluene to dryness. The residue was purified by column chromatography ($SiO_2$, DCM/10% methanol in DCM=0 to 70% in 7 CV) to give the compound 3 (1.39 g, 4.45 mmol, 64% yield) as a white solid. Spectroscopic data matched those for previously reported compound in the literature.

2-(2-(Bis(4-methoxyphenyl)(phenyl)methoxy)ethoxy)ethan-1-amine (5)

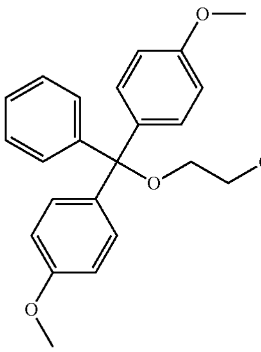

5

To a solution of 2-amino-2-ethoxyethanol (1.50 ml, 14.95 mmol, 1 equiv.) and triethylamine (6.06 ml, 44.86 mmol, 3 equiv.) in dry DCM (75 ml) was slowly added DMT-Cl (10.13 g, 29.9 mmol, 2 equiv.) on ice. The solution was left under stirring at room temperature under Ar for 2 hours. Solvent was evaporated under reduced pressure, residue was resuspended in DCM and ethylthiotetrazole (~1.4 g) was added until a pale pink/orange color appears. Solution was left under stirring for a few minutes. Product was extracted twice with DCM from 10% $Na_2CO_3$ aqueous solution, washed once with a 10% $Na_2CO_3$ aqueous solution, dried over $MgSO_4$, filtered and solvent was evaporated under reduced pressure (40° C.). The residue was purified by column chromatography (Solid loading on celite, $SiO_2$ pretreated with 0.1% TEA in DCM, DCM/TEA (100:0.1) and DCM/MeOH/TEA (90:10:0.1)) to give the compound 5 (4.16 g, 10.2 mmol, 68% yield) as a yellow oil. $^1H$ NMR (500 MHz, $CDCl_3$): δ (ppm) 7.46 (d, J=8 Hz, 2H), 7.36-7.18 (m, 7H), 6.82 (d, J=9 Hz, 4H), 3.78 (s, 6H), 3.64 (t, J=5 Hz, 2H), 3.55 (t, J=5 Hz, 2H), 3.23 (t, J=5 Hz, 2H), 2.90 (t, J=5 Hz, 2H), 2.30 (bs, 2H).

(E)-N-(2-(2-(Bis(4-methoxyphenyl)(phenyl)methoxy)ethoxy)ethyl)-3-(1-((2R,4S,5R)-4-hydroxy-5-(hydroxymethyl)tetrahydrofuran-2-yl)-2,4-dioxo-1,2,3,4-tetrahydropyrimidin-5-yl)acrylamide (6)

6

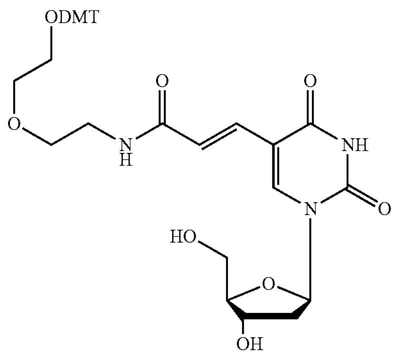

To a 1M NaOH aqueous solution was added 3 (1.39 g, 4.45 mmol, 1 equiv.). The solution was left under stirring overnight, pH was adjusted to 7 with 1M HCl aqueous solution and water was evaporated under reduced pressure (60° C.). Residue was resuspended in acetonitrile and solvent was evaporated under reduced pressure (60° C.). This step was repeated once. Residue was suspended in dry DMF (20 ml). Anhydrous 1-hydroxybenzotriazole (HOBt) (782 mg, 5.79 mmol, 1.3 equiv.) and N-(3-Dimethylaminopropyl)-N'-ethylcarbodiimide hydrochloride (EDC-Cl) (1.11 g, 5.79 mmol, 1.3 equiv.) were successively added. The pale yellow solution was left under stirring for 5 minutes until complete dissolution of EDC-Cl. Compound 5 (1.90 g, 4.67 mmol, 1.05 equiv.) and triethylamine (2.48 ml, 17.8 mmol, 4 equiv.) were then successively added.

The reaction mixture slowly turned cloudy and was left under vigorous stirring overnight. Product was extracted twice with EtOAc from 10% $Na_2CO_3$ aqueous solution, washed once with a 10% $Na_2CO_3$ aqueous solution, dried over $MgSO_4$, filtered and solvent was evaporated under reduced pressure (40° C.). Toluene was used as cosolvent for complete evaporation. The crude product was loaded on celite and purified using the combiFlash system with a "Gold" column pretreated with 0.1% TEA in DCM. DCM/TEA (100:0.1) and DCM/MeOH/TEA (90:10:0.1) were used in a gradient from 0 to 60% in ~8 CV. A pale yellow solid was isolated (1.74 g, 2.53 mmol, 56%). HRMS (ESI-QTOF) m/z: $[M+Na]^+$. Calcd for $C_{37}H_{41}N_3O_{10}Na$ 710.26842; Found 710.26991. $^1H$ NMR (500 MHz, DMSO-d6): δ (ppm) 11.55 (s, 1H), 8.29 (s, 1H), 7.40-7.38 (m, 2H), 7.30 (t, J=8 Hz, 2H), 7.27-7.19 (m, 5H), 7.16-7.02 (m, 2H), 6.88 (d, J=9 Hz, 4H), 6.16 (t, J=7 Hz, 1H), 5.26 (d, J=4 Hz, 1H), 5.16 (t, J=5 Hz, 1H), 4.28-4.26 (m, 1H), 3.82-3.80 (m, 1H), 3.72 (s, 6H), 3.68-3.64 (m, 1H), 3.61-3.56 (m, 3H), 3.49 (t, J=6 Hz, 2H), 3.35-3.32 (m, 2H), 3.06 (t, J=5 Hz, 2H), 2.20-2.12 (m, 2H). $^{13}C$ NMR (126 MHz, $CDCl_3$): δ (ppm) 165.8, 161.8, 158.0, 149.3, 145.0, 142.5, 135.8, 132.3, 129.7, 127.8, 127.7, 126.6, 121.4, 113.2, 109.1, 87.6, 85.3, 84.6, 70.0, 69.5, 69.2, 62.8, 61.0, 55.0.

((2R,3S,5R)-5-(5-((E)-3-((2-(2-(Bis(4-methoxyphenyl)(phenyl)methoxy)ethoxy) ethyl)amino)-3-oxoprop-1-en-1-yl)-2,4-dioxo-3,4-dihydropyrimidin-1(2H)-yl)-3-hydroxytetrahydrofuran-2-yl)methyl 4-oxopentanoate (7)

7

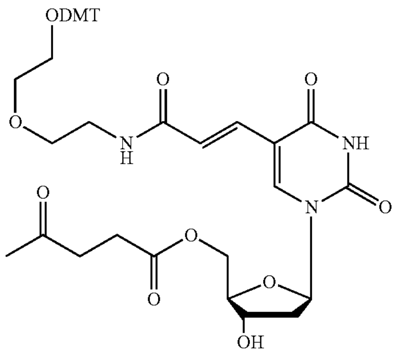

O-(Benzotriazol-1-yl)-N,N,N',N'-tetramethylammonium tetra-fluoroborate (TBTU, 532 mg, 1.66 mmol, 1 equiv.) was dissolved in DMF (2 mL) and N,N-diisopropylethylamine (1.15 mL, 6.63 mmol, 4 equiv.) and stirred at room temperature under Ar in a dry round bottom flask. Freshly distilled levulinic acid (0.17 mL, 1.7 mmol, 1 equiv.) was added, and the reaction was stirred at room temperature for 30 min. Compound 6 (1.14 g, 1.66 mmol, 1 equiv.) was dried under vacuum in a round-bottom flask with a magnetic stirrer. The TBTU/levulinic acid reaction mixture was cannulated to the nucleoside, and the reaction was stirred at room temperature. After 10 h, product was extracted twice with DCM from a saturated $NaHCO_3$ aqueous solution, washed twice with brine, dried over MgSO4, filtered and solvent was evaporated under reduced pressure (40° C.). Toluene was used as cosolvent for complete evaporation. The crude product was loaded on celite and purified using the combiFlash system with a SiO2 "Gold" column pretreated with 0.1% TEA in DCM. DCM and DCM/MeOH (9:1) were used in a gradient from 0 to 50% in ~8 CV. A pale yellow solid was isolated (271 mg, 0.345 mmol, 21%). NB: Addition of TEA in the solvents resulted in poor peak resolution. Nucleoside deprotected with levulinyl and 3'Lev protected were found to have similar shorter retention times than the product. HRMS (APCI-QTOF) m/z: $[M+Cl]^-$ Calcd for $C_{42}H_{47}N_3O_{12}Cl$ 820.28537; Found 820.28403. $^1H$ NMR (500 MHz, $CDCl_3$): δ (ppm) 9.63 (s, 1H), 7.84 (s, 1H), 7.41-7.39 (m, 2H), 7.30-7.14 (m, 10H), 6.79 (d, J=9 Hz, 4H), 6.23 (t, J=6 Hz, 1H), 4.56-4.55 (m, 1H), 4.47-4.44 (m, 1H), 4.26-4.23 (m, 1H), 4.11-4.09 (m, 2H), 3.74 (s, 6H), 3.73-3.53 (m, 6H), 3.27 (t, J=5 Hz, 2H), 2.89-2.83 (m, 1H), 2.79-2.73 (m, 1H), 2.64-2.58 (m, 1H), 2.55-2.45 (m, 2H), 2.25-2.20 (m, 1H), 2.14 (s, 3H). $^{13}C$ NMR (126 MHz, $CDCl_3$): δ (ppm) 207.8, 173.2, 166.8, 162.1, 158.5, 149.1, 145.0, 142.0, 136.3, 132.7, 130.1, 128.3, 127.9, 126.9, 122.8, 113.2, 110.3, 86.3, 85.5, 84.7, 70.8, 70.7, 70.50, 63.1, 55.3, 40.6, 39.6, 38.2, 29.8, 28.2.

Branching Unit (BU)

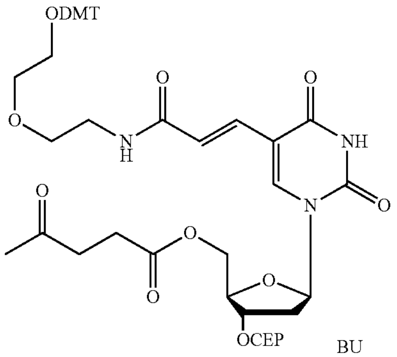

BU

Compound 7 was suspended in acetonitrile and solvent was evaporated under reduced pressure (60° C.). The operation was repeated once and the dried compound was kept under high vacuum for at least 5 hours. In an oven-dried flask, compound 7 (271 mg, 0.345 mmol, 1 equiv.) was then dissolved in anhydrous DCM (5 ml) and 0.30 ml of dry DIPEA (1.7 mmol, 5 equiv.) were added under stirring. CEP-Cl (0.12 ml, 0.52 mmol, 1.5 equiv.) was added slowly and the reaction was allowed to stir under inert gas at room temperature for 2 hours. Two fast extractions with DCM from a $NaHCO_3$ (sat.) aqueous solution were performed. Organic fractions were combined, dried over $MgSO_4$, filtered and the solvent was evaporated under reduced pressure (40° C.). The crude product was loaded on celite and purified using the combiFlash system with a $SiO_2$ "Gold" column pretreated with 1% TEA in DCM. DCM/TEA (100:1) and DCM/MeOH/TEA (90:10:1) were used in a very slow gradient from 0 to 10% in ~10 CV. A white solid was isolated (170 mg, 0.172 mmol, 50%). NB: an impurity thought to be 2-cyanoethyl N,N-diisopropylphosphonamidate ($^{31}P$ NMR signal at 14 ppm) was found to coelute with the product. Purification conditions involving toluene or hexanes and ethyl acetate were not helpful. In the very slow gradient described, the impurity elutes slightly before the product. HRMS (ESI-QTOF) m/z: $[M+Na]^+$ Calcd for $C_{51}H_{64}N_5O_{13}PNa$ 1008.4130; Found 1008.4155. $^1H$ NMR (500 MHz, $CDCl_3$): δ (ppm) 7.84-7.82 (m, 1H), 7.41-7.39 (m, 2H), 7.35-7.13 (m, 10H), 6.79 (d, J=9 Hz, 4H), 6.26-6.22 (m, 1H), 4.52-4.33 (m, 2H), 4.32-4.24 (m, 2H), 3.89-3.83 (m, 1H), 3.78-3.68 (m, 11H), 3.68-3.55 (m, 5H), 3.28 (t, J=5 Hz, 2H), 2.91-2.83 (m, 1H), 2.80-2.73 (m, 1H), 2.69-2.51 (m, 5H), 2.25-2.20 (m, 1H), 2.15, (s, 3H), 1.19-1.17 (m, 12H). $^{13}C$ NMR (126 MHz, $CDCl_3$): δ (ppm) 207.1, 207.0, 172.7, 172.6, 166.6, 162.0, 158.5, 148.9, 145.0, 141.8, 136.3, 132.4, 130.1, 128.3, 127.9, 126.8, 123.1, 117.7, 117.7, 113.2, 110.5, 110.4, 86.3, 85.7, 84.5, 73.0, 72.8, 72.6, 71.0, 70.7, 63.4, 63.3, 63.1, 58.4, 58.4, 58.3, 58.2, 55.3, 46.1, 43.5, 43.4, 40.3, 40.3, 39.5, 38.1, 29.8, 29.8, 28.2, 28.2, 24.8, 24.7, 24.7, 24.6, 20.5, 20.4. $^{31}P$ NMR (203 MHz, $CDCl_3$): δ (ppm) 149.4, 149.3.

9-(Azidomethyl)anthracene (8)

8

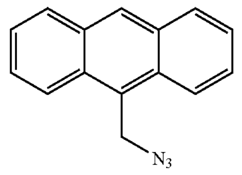

In a dry flask covered with aluminum foil, under an argon atmosphere, to a solution of dimethylformamide (10 mL) were introduced with vigorous stirring, 9-(chloromethyl) anthracene (500 mg, 2.21 mmol, 1 equiv.) and sodium azide (430 mg, 6.62 mmol, 3 equiv.). The reaction was left under vigorous stirring overnight. Distilled water and DCM were added to the reaction medium while pH was not allowed to be under 8.0 with a diluted sodium hydroxide solution. The phases were separated and the aqueous phase was extracted twice with DCM. The combined organic phases were washed once with distilled water and once with brine. Organic phase was dried over magnesium sulfate, filtered under vacuum and the solvent was evaporated (40° C., 50 mbar, 1 h); yielding 400 mg (1.71 mmol, 78%) of a pure yellow solid that was stored away from light. Spectroscopic data matched those for previously reported compound in the literature.

3-(((1-(Anthracen-9-ylmethyl)-1H-1,2,3-triazol-4-yl) methyl)(3-(bis(4-methoxyphenyl) (phenyl)methoxy) propyl)amino)propan-1-ol (9)

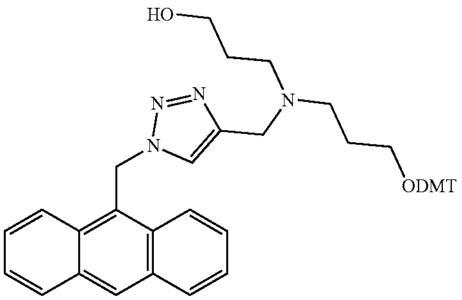

9

In a 10 ml round-bottom flask covered with an aluminum foil, azide 8 (257 mg, 0.80 mmol, 0.95 equiv.) and platform 1 (550 mg, 1.16 mmol, 1 equiv.) were suspended in 1.5 ml $CHCl_3$ and a tBuOH/water (1:1) mixture (12 ml) was added. Freshly prepared solution of sodium ascorbate (46.0 mg, 0.232 mmol, 0.20 equiv.) in 0.3 ml of water and another of copper sulfate (29.0 mg, 0.116 mmol, 0.1 equiv.) in 0.15 ml of water were sequentially added. Reaction was allowed to stir for 6 h at room temperature. Product was extracted twice with DCM from 10% $Na_2CO_3$ aqueous solution, washed once with a 10% $Na_2CO_3$ aqueous solution, dried over $MgSO_4$, filtered and solvent was evaporated under reduced pressure (40° C.). The crude obtained was resuspended in toluene to evaporate remaining tBuOH. 643 mg of a dark yellow/brown solid were obtained (714 mg, 1.01 mmol, 87%). The compound was kept away from light. HRMS (APCI-QTOF) m/z: $[M+Cl]^-$ Calcd for $C_{45}H_{46}N_4O_4Cl$ 741.32131; Found 741.32122. $^1H$ NMR (500 MHz, $CDCl_3$): δ (ppm) 8.56 (s, 1H), 8.26 (d, J=9 Hz, 2H), 8.06 (d, J=8 Hz, 2H), 7.54-7.49 (m, 4H), 7.38-7.37 (m, 2H), 7.27-7.24 (m, 7H), 7.20-7.17 (m, 1H), 7.06 (s, 1H), 6.80 (d, J=9 Hz, 4H), 6.50 (s, 2H), 3.78 (s, 6H), 3.60 (s, 2H), 3.49 (t, J=5 Hz, 2H), 2.99 (t, J=6 Hz, 2H), 2.54 (t, J=6 Hz, 2H), 2.48-2.45 (m, 2H), 1.72-1.66 (m, 2H), 1.55 (quint, J=5 Hz, 2H). $^{13}C$ NMR (126 MHz, $CDCl_3$): δ (ppm) 158.4, 145.3, 144.6, 136.6, 131.5, 130.9, 130.1, 129.9, 129.6, 128.2, 127.8, 127.7, 126.7, 125.5, 124.0, 123.1, 122.1, 113.1, 85.9, 63.9, 61.6, 55.3, 53.6, 51.0, 48.8, 46.6, 28.0, 27.6.

3-(((1-(Anthracen-9-ylmethyl)-1H-1,2,3-triazol-4-yl) methyl)(3-(bis(4-methoxyphenyl) (phenyl)methoxy) propyl)amino)propyl (2-cyanoethyl) diisopropylphosphoramidite (Ant)

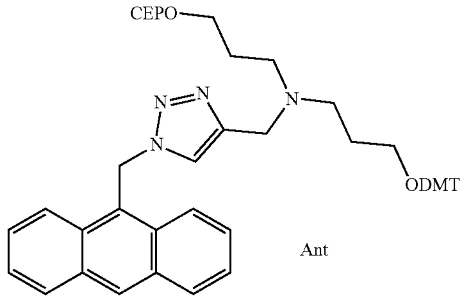

Ant

Compound 9 was suspended in toluene and solvent was evaporated under reduced pressure (60° C.). The operation was repeated once and the dried compound was kept under high vacuum for at least 5 hours. In an oven-dried flask covered with aluminum foil, compound 9 (714 mg, 1.01 mmol, 1 equiv.) was then dissolved in anhydrous DCM (10 ml) and 0.88 ml of dry DIPEA (5.1 mmol, 5 equiv.) were added under stirring. CEP-Cl (0.29 ml, 1.3 mmol, 1.3 equiv.) was added slowly and the reaction was allowed to stir under inert gas at room temperature for 2 hours. Two fast extractions with DCM from a 10% $Na_2CO_3$ aqueous solution were performed. Organic fractions were combined, dried over $MgSO_4$, filtered and the solvent was evaporated under reduced pressure (40° C.). The crude product was loaded on celite and purified using the combiFlash system with a $SiO_2$ "Gold" column pretreated with 1% TEA in hexanes. Hexanes/TEA (100:1) and ethyl acetate were used in a gradient. A white solid was isolated (690 mg, 0.855 mmol, 85%). This compound was stored away from light. HRMS (APCI-QTOF) m/z: $[M+Cl]^-$ Calcd for $C_{54}H_{63}N_6O_5PCl$ 941.42916; Found 941.42839. $^1H$ NMR (500 MHz, $CDCl_3$): δ (ppm) 8.57 (s 1H), 8.26-8.23 (m, 2H), 8.07-8.05 (m, 2H), 7.53-7.47 (m, 4H), 7.37-7.35 (m, 2H), 7.21-7.15 (m, 7H), 7.06 (s, 1H), 6.78 (d, J=9 Hz, 4H), 6.49 (s, 2H), 3.77-3.66 (m, 8H), 3.57 (s, 2H), 3.56-3.44 (m, 4H), 2.94 (t, J=6 Hz, 2H), 2.53 (t, J=6 Hz, 2H), 2.45-2.39 (m, 4H), 1.65-1.58 (m, 4H), 1.14 (d, J=6 Hz, 6H), 1.06 (d, J=7 Hz, 6H). $^{13}C$ NMR (126 MHz, $CDCl_3$): δ (ppm) 158.4, 145.7, 145.4, 136.7, 131.6, 130.9, 130.1, 129.9, 129.5, 128.3, 127.8, 127.7, 126.7, 125.5, 124.1, 123.2, 121.9, 117.8, 113.1, 85.8, 62.0, 61.9, 61.6, 58.5, 58.3, 55.3, 50.9, 50.4, 49.1, 46.6, 43.1, 43.0, 28.8, 28.7, 27.7, 24.8, 24.7, 24.7, 24.6, 20.5, 20.4. $^{31}P$ NMR (203 MHz, $CDCl_3$): δ (ppm) 147.2.

Methyl N-(3-(bis(4-methoxyphenyl)(phenyl) methoxy)propyl)-N-(3-hydroxypropyl)glycyl-L-histidinate (10)

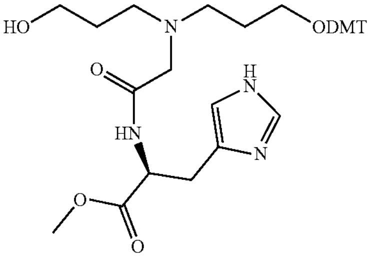

10

Compound PT2b (484 mg, 0.88 mmol, 1 equiv.) was dissolved in about 2 ml of methanol. To the mixture was added 25 ml of 0.4M NaOH in MeOH/water 4:1. The reaction mixture was left under stirring for 3 h at 65° C. Reaction was monitored by TLC. When the higher mobility spot disappeared, methanol was evaporated under reduced pressure (60° C.) until a precipitate appears but a small amount of water remains. DCM is added to the obtained solution and 2 equiv. of tetrabutylammonium chloride (489 mg, 1.76 mmol) were added. Two extractions with DCM from sat. $Na_2CO_3$ solution were performed followed by one washing with 10% $Na_2CO_3$ solution. Organic fractions were combined, dried over $MgSO_4$, filtered and the solvent was evaporated under reduced pressure (40° C.). The tetrabutylammonium carboxylate salt obtained was suspended in anhydrous DMF (5 ml). Anhydrous HOBt (154 mg, 1.14 mmol, 1.3 equiv.) and EDC-Cl (219 mg, 1.14 mmol, 1.3 equiv.) were successively added under argon. The solution was left under stirring for 5 minutes until complete dissolution of EDC-Cl. Histidine methyl ester dihydrochloride (224 mg, 0.92 mmol, 1.05 equiv.) and triethylamine (0.61 ml, 4.4 mmol, 5 equiv.) were then successively added. The reaction mixture was left under vigorous stirring overnight. Product was extracted twice with DCM from 10% $Na_2CO_3$ aqueous solution, washed once with a 10% $Na_2CO_3$ aqueous solution, dried over $MgSO_4$, filtered and solvent was evaporated under reduced pressure (60° C.). The crude product was loaded on celite and purified using the combiFlash system with a SiO2 "Gold" column pretreated with 0.1% TEA in DCM. DCM/TEA (100:0.1) and DCM/Methanol/TEA (90:10:0.1) were used in a gradient. Product was extracted again to remove triethylammonium salts, twice with DCM from 10% $Na_2CO_3$ aqueous solution, washed once with a 10% $Na_2CO_3$ aqueous solution, dried over $MgSO_4$, filtered and solvent was evaporated under reduced pressure (60° C.). A white solid was isolated (233 mg, 0.361 mmol, 41%). LRMS: Calc. exact mass: 644.32 g/mol. Measured (positive mode): 667.2 (M+23). $^1H$ NMR (500 MHz, $CDCl_3$): δ (ppm) 9.17 (bs 1H), 8.16 (bs, 1H), 7.47 (d, J=1 Hz, 1H), 7.40-7.39 (m, 2H), 7.29-7.26 (m, 6H), 7.22-7.18 (m, 1H), 6.81 (d, J=9 Hz, 4H), 6.77 (s, 1H), 4.86-4.82 (m, 1H), 3.79 (s, 6H), 3.73-3.69 (m, 5H), 3.14-3.04 (m, 6H), 2.62-2.54 (m, 4H), 1.73-1.65 (m, 4H). $^{13}C$ NMR (126 MHz, DMSO): δ (ppm) 171.6, 170.7, 157.9, 145.2, 136.0, 135.0, 129.6, 127.8, 127.6, 126.6, 113.1, 85.2, 61.2, 58.9, 57.9, 55.0, 51.8, 51.6, 51.4, 45.7, 30.0, 27.2.

Methyl N-(3-(bis(4-methoxyphenyl)(phenyl)methoxy)propyl)-N-(3-(((2-cyanoethoxy) (diisopropylamino)phosphanyl)oxy)propyl)glycyl-L-histidinate (His)

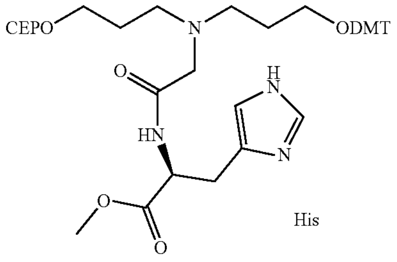

His

Compound 10 was suspended in acetonitrile and solvent was evaporated under reduced pressure (60° C.). The operation was repeated once and the dried compound was kept under high vacuum for at least 5 hours. In an oven-dried flask, compound 10 (154 mg, 0.239 mmol, 1 equiv.) was then dissolved in anhydrous DCM (5 ml) and 0.21 ml of dry DIPEA (1.2 mmol, 5 equiv.) were added under stirring. CEP-Cl (0.06 ml, 0.2 mmol, 1.1 equiv.) was added slowly and the reaction was allowed to stir under inert gas at room temperature for 2 hours. Two fast extractions with DCM from a 10% $Na_2CO_3$ aqueous solution were performed. Organic fractions were combined, dried over $MgSO_4$, filtered and the solvent was evaporated under reduced pressure (40° C.). The crude product was loaded on celite and purified using the combiFlash system with a $SiO_2$ "Gold" column pretreated with 1% TEA in hexanes. Hexanes/TEA (100:1) and ethyl acetate were used in a gradient. A white solid was isolated (110 mg, 0.130 mmol, 54%). HRMS (ESI-QTOF) m/z: $[M+Na]^+$ Calcd for $C_{45}H_{61}N_6O_8PNa$ 867.4181; Found 867.4164. $^1H$ NMR (500 MHz, $CDCl_3$): δ (ppm) 9.41 (bs 1H), 8.04 (bs, 1H), 7.47 (s, 1H), 7.40-7.39 (m, 2H), 7.29-7.26 (m, 6H), 7.21-7.18 (m, 1H), 6.81 (d, J=9 Hz, 4H), 6.73 (s, 1H), 4.80-4.77 (m, 1H), 3.88-3.55 (m, 15H), 3.11-3.03 (m, 6H), 2.63-2.52 (m, 6H), 1.72-1.63 (m, 4H), 1.17 (t, J=6 Hz, 12H). $^{13}C$ NMR (126 MHz, $CDCl_3$): δ (ppm) 158.5, 145.3, 136.6, 135.2, 130.1, 128.3, 127.9, 126.8, 113.2, 86.0, 62.0, 61.7, 58.7, 58.2, 58.1, 58.0, 55.3, 53.0, 52.9, 52.6, 52.4, 52.2, 51.8, 51.1, 45.6, 43.2, 43.1, 29.8, 29.4, 28.1, 24.8, 24.8, 24.8, 24.7, 20.6, 20.6. $^{31}P$ NMR (203 MHz, $CDCl_3$): δ (ppm) 147.6 147.4.

Methyl N-(3-(bis(4-methoxyphenyl)(phenyl)methoxy)propyl)-N-(3-hydroxypropyl)glycyl-L-tryptophanate (11)

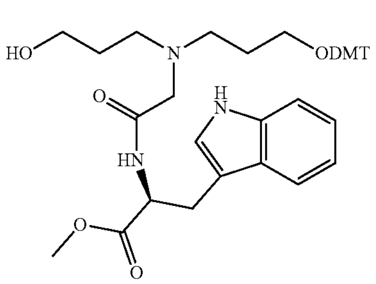

11

Compound PT2b (484 mg, 0.88 mmol, 1 equiv.) was dissolved in about 2 ml of methanol. To the mixture was added 25 ml of 0.4M NaOH in MeOH/water 4:1. The reaction mixture was left under stirring for 3 h at 65° C. Reaction was monitored by TLC. When higher mobility spot disappeared, methanol was evaporated under reduced pressure (60° C.) until a precipitate appears but a small amount of water remains. DCM is added to the obtained solution and 2 equiv. of tetrabutylammonium chloride (489 mg, 1.76 mmol) were added. Two extractions with DCM from sat. $Na_2CO_3$ solution were performed followed by one washing with 10% $Na_2CO_3$ solution. Organic fractions were combined, dried over $MgSO_4$, filtered and the solvent was evaporated under reduced pressure (40° C.). The tetrabutylammonium carboxylate salt obtained was suspended in DMF (5 ml). Anhydrous HOBt (154 mg, 1.14 mmol, 1.3 equiv.) and EDC-Cl (219 mg, 1.14 mmol, 1.3 equiv.) were successively added. The solution was left under stirring for 5 minutes until complete dissolution of EDC-Cl. Tryptophan methyl ester hydrochloride (235 mg, 0.92 mmol, 1.05 equiv.) and triethylamine (0.61 ml, 4.4 mmol, 5 equiv.) were then successively added. The reaction mixture was left under vigorous stirring overnight. Solvent was evaporated under reduced pressure (60° C.). The crude product was loaded on celite and purified using the combiFlash system with a $SiO_2$ "Gold" column pretreated with 0.1% TEA in DCM. DCM/TEA (100:0.1) and DCM/Methanol/TEA (90:10:0.1) were used in a gradient. A pale yellow solid was isolated (260 mg, 0.374 mmol, 43%). HRMS (ESI-QTOF) m/z: $[M+H]^+$ Calcd for $C_{41}H_{48}N_3O_7$ 694.34868; Found 694.34783. $^1H$ NMR (500 MHz, $CDCl_3$): δ (ppm) 8.36 (s, 1H), 7.66 (d, J=8 Hz, 1H), 7.52 (d, J=8 Hz, 1H), 7.43-7.41 (m, 2H), 7.31-7.21 (m, 8H), 7.13 (t, J=7 Hz, 1H), 7.08 (t, J=7 Hz, 1H), 6.92 (d, J=2 Hz, 1H), 6.83 (d, J=9 Hz, 4H), 4.92-4.88 (m, 1H), 3.78 (s, 6H), 3.68 (s, 3H), 3.38-3.26 (m, 4H), 3.09-2.96 (m, 4H), 2.34-2.52 (m, 4H), 1.63-1.52 (m, 2H), 1.47-1.39 (m, 2H). $^{13}$C NMR (126 MHz, $CDCl_3$): δ (ppm) 172.7, 171.7, 158.4, 145.3, 136.5, 136.2, 130.1, 128.2, 127.9, 127.7, 126.8, 122.9, 122.2, 119.6, 118.6, 113.1, 111.3, 109.9, 86.0, 61.5, 60.5, 58.7, 55.3, 52.5, 52.5, 52.1, 52.0, 30.1, 27.8, 27.4.

Methyl N-(3-(bis(4-methoxyphenyl)(phenyl) methoxy)propyl)-N-(3-(((2-cyanoethoxy) (diisopropylamino)phosphanyl)oxy)propyl)glycyl-L-tryptophanate (Trp)

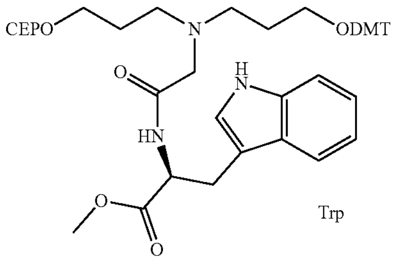

Trp

Compound 11 was suspended in acetonitrile and solvent was evaporated under reduced pressure (60° C.). The operation was repeated once and the dried compound was kept under high vacuum for at least 5 hours. In an oven-dried flask, compound 11 (254 mg, 0.353 mmol, 1 equiv.) was then dissolved in anhydrous DCM (6 ml) and 0.31 ml of dry DIPEA (1.8 mmol, 5 equiv.) were added under stirring. CEP-Cl (0.10 ml, 0.46 mmol, 1.3 equiv.) was added slowly and the reaction was allowed to stir under inert gas at room temperature for 2 hours. Two fast extractions with DCM from a 10% $Na_2CO_3$ aqueous solution were performed. Organic fractions were combined, dried over $MgSO_4$, filtered and the solvent was evaporated under reduced pressure (40° C.). The crude product was loaded on celite and purified using the combiFlash system with a $SiO_2$ "Gold" column pretreated with 1% TEA in hexanes. Hexanes/TEA (100:1) and ethyl acetate were used in a gradient. A white solid was isolated (286 mg, 0.320 mmol, 91%). HRMS (ESI-QTOF) m/z: $[M+H]^+$ Calcd for $C_{50}H_{65}N_5O_8P$ 894.45653; Found 894.45527. $^1$H NMR (500 MHz, $CDCl_3$): δ (ppm) 8.54 (s, 1H), 7.72 (d, J=8 Hz, 1H), 7.50 (d, J=8 Hz, 1H), 7.41-7.40 (m, 2H), 7.29-7.19 (m, 8H), 7.11 (t, J=7 Hz, 1H), 7.05 (t, J=7 Hz, 1H), 6.92 (m, 1H), 6.81 (d, J=9 Hz, 4H), 4.88-4.85 (m, 1H), 3.83-3.69 (m, 8H), 3.64 (s, 3H), 3.62-3.42 (m, 4H), 3.35-3.24 (m, 2H), 3.06-2.95 (m, 4H), 2.55 (t, J=5 Hz, 2H), 2.49-2.44 (m, 4H), 1.55-1.47 (m, 4H), 1.20-1.15 (m, 12H). $^{13}$C NMR (126 MHz, $CDCl_3$): δ (ppm) 172.1, 171.5, 158.3, 145.2, 136.4, 136.4, 136.1, 129.9, 128.1, 127.7, 127.5, 126.6, 122.8, 121.9, 119.3, 118.4, 117.8, 117.8, 113.0, 111.3, 109.7, 109.7, 85.8, 61.8, 61.7, 61.6, 61.6, 61.3, 58.5, 58.5, 58.2, 58.1, 58.0, 58.0, 55.1, 52.6, 52.4, 52.2, 52.0, 43.0, 42.9, 29.0, 28.9, 27.9, 27.8, 27.4, 24.6, 24.6, 24.6, 24.6, 20.3, 20.3. $^{31}$P NMR (203 MHz, $CDCl_3$): δ (ppm) 147.5 147.4.

1-(Bis(4-methoxyphenyl)(phenyl)methoxy)dodecan-2-yl (2-cyanoethyl) diisopropylphosphoramidite (Bal)

Bal

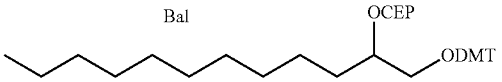

2 steps protocol to obtain Bal from 1,2-dodecanediol and characterization data are detailed elsewhere (Laing et al., 2015, Chembiochem, 16: 1284-1287).

EXAMPLE II

Solid-Phase Synthesis

For unbranched oligomers, synthesis was performed on a 1 μmol scale, starting from a universal 1000 Å LCAA-CPG solid support. 5'-DMT and 5'-Lev nucleoside phosphoramidites (benzoyl protected adenosine, benzoyl protected cytidine, isobutyryl protected guanosine and thymidine) were dissolved in dry acetonitrile and coupling times of 3 minutes were used. Molecular trap packs were used to maintain the acetonitrile, the activator and the phosphoramidite solutions dry. Removal of the DMT protecting group was carried out using 3% dichloroacetic acid in dichloromethane on the DNA synthesizer. Removal of the Levulinyl protecting group was carried out using hydrazine hydrate (50-60%) diluted to 0.5M in a 3:2 (v:v) pyridine/acetic acid solution. Hydrazine treatment lasts 6 minutes with three injections of 2 minutes each unless otherwise noted.

For branched oligomers, synthesis was performed similarly starting from a universal 2000 Å LCAA-CPG solid support and using coupling times of 10 minutes. The codons were synthesized after the unnatural monomer couplings in the case of the library but before otherwise.

Under a nitrogen atmosphere in a glove box (<2.5 ppm trace moisture), in a 10 ml oven-dried round bottom flask, monoprotected alcohol 2 (12 mg, 0.030 mmol) is dissolved in dry DCM (300 μL). Diisopropylethylamine (4.8 μL, 0.050 mmol, 1 eq.) and N,N-Diisopropylamino cyanoethyl phosphonamidic-Cl (6.0 μL, 0.027 mmol, 0.9 eq.) are added. Reaction is allowed to stir at room temperature during 45 minutes. Coupling was done using the 'syringe' technique: the crude solution containing the phosphoramidite (200 μL, 0.1 M) is mixed with the standard activator solution (200 μL, 0.25 M) in presence of the CPG using syringes. After ten minutes, the solution was removed from the columns and the strands underwent capping, oxidation and deblocking steps in the synthesizer.

Sequences without unnatural monomers underwent classical deprotection procedures:

completed syntheses were cleaved from the solid support and deprotected in 28% aqueous ammonium hydroxide solution for 16-18 hours at 65° C. Deprotection involving methylamine is not compatible with benzoyl-protected cytidine. The crude product solution was separated from the solid support and concentrated under reduced pressure at 60° C. This crude solid was re-suspended in Millipore water before further RP-HPLC or gel purification.

With unnatural monomers, a 1:3 tert-butylamine/water solution during 6 h at 65° C. was performed first to cleanly deprotect methyl esters into carboxylate. This step was followed by the standard deprotection procedure in ammonium hydroxide to make sure deprotection is complete.

TABLE 3

Sequence of strands used, and special synthetic conditions..

| Strand name | Sequence (5′ to 3′) | Special synthetic conditions |
|---|---|---|
| AT | TTTTTCAGTTGACCATATA (SEQ ID NO: 1) | — |
| HYD1 | ACGACGACGACGACGACGACGACGACGACGACGACGACGAC<br>GCG (SEQ ID NO: 2) | 30 first couplings followed by hydrazine treatments of 10 min |
| LEV1 | T***TTT***T***TTTT***G***TTCC***T***AACC***G (SEQ ID NO: 3) | 1.5 M hydrazine, 10 min |
| LEV2 | T***TT***T***TTTT***G***TTCC***G (SEQ ID NO: 4) | Hydrazine 32 min |
| T10 | GG***TCCT***AAT***G***C***C***GATCGA (SEQ ID NO: 5) | Hydrazine 10 min |
| T30 | GG***TCCT***AAT***G***C***C***GATCGA (SEQ ID NO: 6) | Hydrazine 30 min |
| DNA 21 mer | TTTTTCAGTTGACCATATA-X-***A***T (SEQ ID NO: 7) | From X, 20 hydrazine treatments of 10 min |
| BR1 | CGTCGAGGCCC***GGGAAGAAAGGA***-BU-<br>ACACGTCACGCCTTTTTTTTT<br>Branch: TCGA (SEQ ID NO: 8) | Hydrazine 20 min |
| BR2 | CGTCGAGGCCC***GGGAAGAAA***-BU-GCATAGGATACACGTCACGCC<br>(SEQ ID NO: 9)<br>Branch: TCGA | Hydrazine 20 min |
| BR3 | DMT-CGTCGAGGCCC***TTAATTGGTTCCTTAACCTTAGGA***-BU-<br>ACACGTCACGCCTTTTTTTTT (SEQ ID NO: 10)<br>Branch: TATGTCTACT | Hydrazine 15 min |
| TBA1 | CGTCGAGGCCC***CTTCTTCTTCGTCTTCTTCTTAGGA***-BU-<br>ACACGTCACGCCTTTTTTTTT<br>Branch: GGTTGGTGTGGTTGGTTTTT (SEQ ID NO: 11) | Hydrazine 10 min |
| TBA2 | CGTCGAGGCCC***GTGCTTACCCGTGACCTTCTTAGGA***-BU-<br>ACACGTCACGCCTTTTTTTTT<br>Branch: GG**His**TGG**C12**GTGG**Alk**TGGTTTTT (SEQ ID NO: 12) | Hydrazine 10 min |
| TBA3 | CGTCGAGGCCC***ATACAGGTATAATGCCATTGAAGGA***-BU -<br>ACACGTCACGCCTTTTTTTTT<br>Branch: GG**TrpSug**GG**PheAnt**TGG**Bal**AGG**Nap**TTTT (SEQ ID NO: 13) | Hydrazine 10 min |
| TBA1F | CGTCGAGGCCC***CTTCTTCTTCGTCTTCTTCTTAGGA***-BU-<br>ACACGTCACGCCTTTTTTTTT<br>Branch: 6FAM-GGTTGGTGTGGTTGGTTTTT (SEQ ID NO: 14) | Hydrazine 10 min |
| TBA2F | CGTCGAGGCCC***GTGCTTACCCGTGACCTTCTTAGGA***-BU-<br>ACACGTCACGCCTTTTTTTTT<br>Branch: 6FAM-GGTTGG**C12**GTGG**Alk**TGGTTTTT (SEQ ID NO: 15) | Hydrazine 10 min |
| TBA3F | CGTCGAGGCCC***ACGCAGGTATAATGCCATTGAAGGA***-BU-<br>ACACGTCACGCCTTTTTTTTT<br>Branch: 6FAM-GG**DelPhe**GG**PheAnt**TGG**Bal**AGG**Nap**TTTT (SEQ ID NO: 16) | Hydrazine 10 min |
| Forward Primer | ACACTGACGACATGGTTCTACACGTCGAGGCCC (SEQ ID NO: 17) | |
| Reverse Primer | TACGGTAGCAGAGACTTGGTCTGGCGTGACGTGTATCCT (SEQ ID NO: 18) | |
| LIB | CGTCGAGGCCC ***NNN NNN NNN NNN NNNNNN NNN AGGA***-BU-<br>ACACGTCACGCCTTTTTTTTT<br>Branch: GG 7 6 GG 5 4 TGG 3 2 GG 1 TTTT (SEQ ID NO: 19) | |

TABLE 3-continued

| Sequence of strands used, and special synthetic conditions.. | | |
|---|---|---|
| Strand name | Sequence (5' to 3') | Special synthetic conditions |
| PC | 6FAM-GGTTGGTGTGGTTGG (SEQ ID NO: 20) | |
| NCS | 6FAM-GGTTGGTGTTGTTTG (SEQ ID NO: 21) | |
| NCL | 6FAM-CGTCGAGGCCCCTTCTTCTTCGTCTTCTTCTTAGGATACACGT CACGCCTTTTTTTTT (SEQ ID NO: 22) | |

Letters in bold and italic indicate the use of 5'-Levulinyl amidites

TABLE 4

| Monomers used during library synthesis. | | | | | | |
|---|---|---|---|---|---|---|
| Position modified | Aliquot A | Aliquot B | Aliquot C | Aliquot D | Aliquot E | Aliquot F |
| 1 | G | T | Alk | C12 | Nap | Phe |
| 2 | A | T | Alk | C12 | Sug | Trp |
| 3 | C | T | Ant | Nap | Phe | Trp |
| 4 | A | G | Alk | C12 | Nap | Sug |
| 5 | G | T | C12 | Phe | Sug | Trp |
| 6 | A | T | Alk | His | Nap | Phe |
| 7 | G | T | Ant | C12 | Sug | Trp |

Analysis and purification with the HPLC were performed as follows. Solvents (0.22 μm filtered): 50 mM triethylammonium acetate (TEAA) buffer (pH 8.0) and HPLC grade acetonitrile. All gradients were followed by a short column wash in 95% acetonitrile. Column: Hamilton PRP-C18 5 μm 100 Å 2.1×150 mm. For each analytical separation approximately 0.5 OD260 of crude DNA was injected as a 20-50 μL solution in Millipore water. Detection was carried out using a diode-array detector, monitoring absorbance at 260 nm.

Denaturing Polyacrylamide Gel Electrophoresis (PAGE) was carried out at room temperature for 30 minutes at 250V followed by 1 hour at 500V with big plates and only for 1 h at 100V with small plates. TBE buffer (1×) was used and the concentration of urea in the gel was 7M. For each lane 5 μL of DNA (0.1 to 2 μM) in water was added to 5 μL of 8 M urea. The DNA bands for all gels were visualized by incubation with GelRed™. In all gels, the ladder used is the Invitrogen Ultra Low Range ladder.

The oligomers were analyzed by LC-ESI-MS in negative ESI mode. Samples (~60 pmols in $H_2O$) were run through an Acclaim RSLC 120 C18 column (2.2 μm, 120 Å 2.1×50 mm) using a gradient of mobile phase A (100 mM 1,1,1,3,3,3-hexafluoro-2-propanol and 5 mM triethylamine in water) and mobile phase B (Methanol) in 8 minutes (2% to 100% B). Liquid chromatography was performed as a control for strand purity which was found to be superior to 90% in all cases.

TABLE 5

| ESI-MS characterization of the strands synthesized. | | |
|---|---|---|
| Strand | Expected exact mass (g/mol) | Found exact mass (g/mol) |
| AT-2-Nap | 6491.23 | 6491.34 |
| LEV1 | 6027.00 | 6026.98 |
| LEV2 | 4214.70 | 4215.76 |
| BR1 | 15230.90 (MW) | 15230.20 (MW) |
| BR2 | 14346.39 (MW) | 14345.68 (MW) |
| BR3-DMToff | 20590.40 (MW) | 20589.71 (MW) |

TABLE 5-continued

| ESI-MS characterization of the strands synthesized. | | |
|---|---|---|
| Strand | Expected exact mass (g/mol) | Found exact mass (g/mol) |
| BR3, bottom band[a] | 6310.06 | 6310.00 |
| BR3, middle band[a] | 9810.66 | 9810.47 |
| BR3, HPLC fraction 4[a] | >20590 | Mostly >27000 |
| AT-Ant | 6231.17 | 6231.25 |
| AT-Bal | 6029.14 | 6029.22 |
| AT-His | 6155.12 | 6155.22 |
| AT-Trp | 6204.14 | 6204.25 |
| TBA1 | 24042.59 (MW) | 24041.20 (MW) |
| TBA2 | 24110.81 (MW) | 24109.73 (MW) |
| TBA3 | 24839.97 (MW) | 24839.96 (MW) |

MW stands for molecular weight.
[a]These strands are byproducts from BR3 synthesis.

Polymerase chain reaction (PCR) was carried out using the MyTaq™ HS Red Mix PCR kit. The reaction was performed in a batch of 60 μL, using 0.1 ng·μL$^{-1}$ of template (except for 1×10$^{-5}$ ng·μL-1 of TBA3), 0.625 μM of each of the forward and reverse primers, and a final concentration of 1× MyTaq™ HS Red Mix. The mixture was then heated at 95° C. for 1 minute and was followed by 30 cycles of: 1) 95° C. for 15 seconds, 2) 60-67° C. (temperature was optimized depending on the sample) for 15 seconds, and 3) 72° C. for 15 seconds. After PCR, the samples were purified using a QIAquick PCR Purification Kit (manufacturer protocol was followed). Electrophoresis gel experiments were performed in native and denaturing conditions.

Sequencing was performed by the McGill University and Génome Québec Innovation Center. Methodology for MiSeq Illumina next generation sequencing sample preparation is indicated below.

The barcoding step adds an index (or barcode) to each sample and the sequence of Illumina adapters required for DNA binds to flow cell (i5 and i7).

TABLE 6

| Master Mix components for barcoding step. | | | |
|---|---|---|---|
| Master Mix Components | 1× | 8 | Final Concentration |
| Roche PCR 10× Buffer without $MgCl_2$ | 2.000 | 16.0 | 1× |
| Roche $MgCl_2$ 25 mM | 1.438 | 11.5 | 1.8 mM |
| Roche DMSO | 1.000 | 8.0 | 5% |
| dNTP mix 10 mM FroggaBio | 0.400 | 3.2 | 0.2 mM |
| TAQ 5 U-ul Roche FastStart High Fi | 0.100 | 0.8 | 0.025 U/ul |
| $H_2O$ | 12.063 | 96.5 | |

Polymerase chain reaction (PCR) was carried out using 17 μL of the Master Mix for a 20 μL final volume. The reaction was performed using ~0.1 ng·μL$^{-1}$ of template (except for 1×10$^{-5}$ ng·μL-1 of TBA3), 0.2 μM of each of the forward and reverse primers with the barcode corresponding to each sample. The mixture was then heated at 95° C. for 10 minutes and was followed by 15 cycles of: 1) 95° C. for 15 seconds, 2) 60° C. for 15 seconds, and 3) 72° C. for 15 seconds. The cycles were followed by 3 minutes at 72° C.

All amplicons had a similar profile on agarose gel so no quantification was necessary to generate the pool (library). The library was then generated by pooling 5 ul of each sample except for sample TBA3 (7 ul) in order to get more reads for this sample.

Final Steps:

- Cleaning-up of the pool (or library) with a ratio of 1.5 of sparQ PureMag Beads (from Quantabio).
- QC of the library as follows: library was quantified by fluorescence using Qubit dsDNA high-sensitivity (HS) kit (ThermoFisher). Average fragment size was estimated on 2% agarose gel with 100 bp DNA ladder.
- The library was added to the "principal" library at a ratio of 1% of the MiSeq lane. 10% of Phix control library was spiked into the final amplicon pools (loaded at a final concentration of 10 pM) to improve the unbalanced base composition. Sequencing with the MiSeq Reagent Kit v2 500 cycles from Illumina. Sequencing was done with LNA™ modified custom primers (Exiqon):

```
Primer read1: LNA-CS1:
                                    (SEQ ID NO: 23)
ACACTGACGACATGGTTCTACA

Primer read2: LNA-CS2:
                                    (SEQ ID NO: 24)
TACGGTAGCAGAGACTTGGTCT

Primer index read: LNA-CS2rc:
                                    (SEQ ID NO: 25)
AGACCAAGTCTCTGCTACCGTA
```

Results were obtained as 2 FASTQ files per sample containing the forward strand read and the reverse strand read. The forward strand reads were used for BR1 and BR2 to count the number of times code sequences were found as well as the number of times the forward primer region sequence (5'-CGTCGAGGCCC-3'; (SEQ ID NO: 26) was found.

For BR3, TBA1, TBA2, TBA3, the reverse strand was privileged read in order to count the number of times the reverse primer region was found (5'-GGCGTGACGTGTATCCT-3'; (SEQ ID NO: 28). It is a 17mer which is closer in length and therefore more comparable to the code sequences' length (20mer for BR3 and 21mer for TBA1, TBA2 and TBA3). The number of times the complementary code sequence was found was also counted. Ratio of reads found/total number of reads are reported in Table 1. Using the reads of the complementary strand led to similar results.

The fluorescence polarization assay was based on the following. All model compounds were synthesized as described above. Sequences for TBA1F, TBA2F, TBA3F, NCS, NCL, and PC are in Table 3. Each model compound was dissolved in thrombin binding buffer (20 mM Tris, 140 mM NaCl, 20 mM KCl, 1 mM $CaCl_2$, 1 mM $MgCl_2$, 0.1% Triton X) to a concentration of 10 nM and stored in freezer in the dark until further use. For the assay, the model compounds were thawed, then heated at 95° C. for 4 minutes, then cooled at 4° C. for 15 minutes. Thrombin (T6684, Sigma Aldrich) was prepared fresh each time by dissolving the entire vial with 200 μL thrombin binding buffer, then measuring the absorbance on the NanoDrop Lite spectrophotometer, and calculating the concentration using E1%/280, 18.3. Dilutions of thrombin were made at 2× concentration in thrombin binding buffer and were kept on ice before use. Next, 30 μL of each model compound and 30 μL of each thrombin dilution were mixed separately in a 96-well Black/Clear Flat Bottom microplate. The plate was shaken on a Cytation 5 Cell Imaging Multi-Mode Reader (BioTek) plate reader and incubated at room temperature for 20 minutes. Finally, polarization was measured for each sample with the following parameters: light source—Xenon Flash, excitation at 485 nm, emission at 528 nm and sensitivity set to 90%. The change in polarization, defined as the different between the polarization value measured in the absence of thrombin and the presence, was plotted against the total concentration of thrombin. A binding isotherm was fit using GraphPad Prism 6 using which one site binding (hyperbola) fit. $K_d$ values were reported as the mean and standard deviation of three independent experiments.

EXAMPLE III

Library Selection and Sequencing

The DNA-encoded polymer libraries included both Libfluo, a fluorescently-tagged library and Lib, a non-fluorescent version of the same library. Both were screened separately for functional binding to thrombin using the same steps and the non-fluorescent library was screened twice, to determine reproducibility. The polymer library (0.2 nmol) was suspended in 200 μL of selection buffer, mixed with 0.1 mg/mL of sheared salmon sperm DNA, then denatured at 95° C. for 4 min, cooled on ice for 10 min and incubated at RT for 30 min. Three columns were prepared in a microcentrifuge tube spin-filter: 20 mg agarose as a negative agarose selection column, 100 μL of streptavidin agarose slurry as a counter-selection column and 100 μL of thrombin agarose slurry as a positive column. All three were washed 5 times with the selection buffer prior to the screening on low centrifugation settings (2000 rpm or 367×g). To start the screening, the DNA library solution was incubated first with the negative column, the flow-through collected was immediately incubated with the counter-selection column. The flow-through from the counter-selection column was incubated with the positive thrombin column. The final flow-through was discarded (or kept for monitoring the enrichment in case of fluorescent library), and the column was washed 6 times with selection buffer. Further elution steps included washing the column with the 1 μM of the original thrombin-binding aptamer in a competitive displacement as well as free thrombin in excess (10 μM). The fluorescence of all washes and fractions was measured where applicable, and elutions were amplified and sent for sequencing.

The combinatorial library of DNA-encoded aptamers was tested in the presence of thrombin. Traditional SELEX experiments typically rely on 5-20 cycles of binding, separation and amplification in order to achieve sufficient enrichment of strongly-binding aptamers. However, there is precedent for the selection of aptamers with only one round of amplification. Two strategies of interest were i) one stringent separation step with amplification and sequencing carried out on multiple isolated fractions and ii) repeated rounds of selection without aptamer elution or amplification. As only the DNA barcode of the aptamer-code construct of the present disclosure can be amplified by PCR, selection was carried out on the DNA-encoded library and samples were taken at different stages of the selection process for amplification and sequencing. Increasingly stringent selection steps were used to collect different samples of potential aptamers. After removing non-specific binders with agarose devoid of thrombin, the library was tested in the presence of thrombin immobilized on agarose. After washes with buffer solution to remove unbound aptamers, the columns were subject to two consecutive elutions with solutions containing the unmodified thrombin aptamer (without primers or a DNA-code), with outcompeted samples collected for sequencing after each elution. The columns were then eluted with free thrombin in solution in order to remove the aptamers still bound to the immobilized thrombin. Library samples were obtained prior to screening. A fluorescently tagged library was also tested with the same conditions and steps. After PCR amplification, the amplicons obtained were indexed and sequenced through MiSeq next-generation sequencing according to standard procedures. Each sequence was read between 30,000 and 50,000 times. Fastq files were obtained and analyzed to condense the full sequence including primers down to the 21mer DNA barcode. FASTAptamer is a bioinformatics toolkit useful for processing high-throughput sequencing data obtained from aptamer selections. Fastaptamer was used to determine the most common sequences of modified aptamers. Table 7 below presents the three most popular sequences in each sample, with the sequence shown being of the modified sites from 5' to 3' (5' GG 76 GG 54T GG 32 GG 1 3') and the normal bases at these sites shown for the traditional TBA with a 3' T.

TABLE 7

The three most popular sequences for each sample are shown with their read counts and normalized abundances (in reads per million).

| Sample | Most popular sequences (5' to 3') | | | | | | | Reads per million |
|---|---|---|---|---|---|---|---|---|
| | 7 | 6 | 5 | 4 | 3 | 2 | 1 | |
| TBA | T | T | T | G | T | T | T | — |
| Library | Trp | A | C12 | Nap | Nap | T | G | 639 |
| | G | T | C12 | G | Nap | C12 | G | 578 |
| | Sug | T | Trp | C12 | Nap | C12 | Phe | 548 |
| Library* | G | Phe | Trp | Nap | Nap | C12 | G | 566 |
| | G | A | C12 | A | Phe | C12 | Nap | 503 |
| | T | T | T | G | Phe | C12 | Nap | 503 |
| After 1$^{st}$ elution | T | T | G | G | Phe | T | Nap | 20715 |
| with TBA | G | T | Trp | Sug | Phe | T | Nap | 15892 |
| | T | T | T | C12 | Ant | T | Nap | 12029 |
| After 1$^{st}$ elution | T | T | Phe | C12 | Phe | T | G | 21289 |
| with TBA* | G | T | Phe | C12 | Phe | T | Nap | 16314 |
| | T | T | Trp | G | Trp | T | G | 15945 |
| After 2$^{nd}$ elution | G | T | C12 | C12 | Trp | T | C12 | 33036 |
| with TBA | Trp | T | C12 | C12 | T | T | G | 24532 |
| | G | T | Trp | Sug | Phe | T | Nap | 19841 |
| After 2$^{nd}$ elution | G | T | Phe | C12 | Phe | T | Nap | 25318 |
| with TBA* | Trp | T | C12 | C12 | T | T | Nap | 16998 |
| | Trp | T | Sug | Nap | T | T | C12 | 14012 |
| After elution with | T | T | T | G | T | T | T | 25877 |
| free | G | T | Trp | Sug | Phe | T | Nap | 1840 |
| thrombin | G | T | C12 | C12 | Trp | T | T | 1467 |
| After elution | T | T | T | G | T | T | T | 37117 |
| with free | Sug | T | Phe | G | Nap | C12 | Nap | 3638 |
| thrombin* | Trp | T | Trp | Nap | Nap | C12 | G | 1854 |

Unsurprisingly, the most popular sequences from library samples occur at a much lower relative frequency than the most popular sequences in samples that underwent a form of screening, giving an approximate baseline for normalized abundance (~700 reads per million) to compare with enriched sequences (~10000-30000 reads per million). The samples obtained after elution with free thrombin were more likely to provide the strongest binding aptamers as they had withstood two washes; however, the results showed that the most common sequences by far for these samples were those of the original thrombin binding aptamer, with the next most popular sequences having much fewer reads per million. Consequently, the popularity of sequences in previously obtained samples were used to pick individual sequences of interest for future binding affinity studies. For example, 5' G T Phe C12 Phe T Nap 3' is a sequence that appeared prominently twice—as the most popular for the second elution of the fluorescent library and the first elution of the normal library. Another tendency to notice in the above table is the preference for certain modifications in different positions. Focusing on the non-library samples, there was a strong preference for T in positions 6 and 2, a tendency for C12 in position 4, a tendency for Nap in position 1, and a slight preference for Phe in positions 5 and 3. Samples were also analyzed based on the relative prevalence of a modification in a specific position of the aptamer across all observed sequences. These tendencies are exemplified in Table 8 below, which presents the most common modification in each position for all sequences from a given sample.

TABLE 8

The relative frequency (in %) of the most observed modification (mod) at a certain position across all sequences from a given sample. Asterisks (*) denote the library was fluorescently tagged. Bolded entries indicate that the next most common modification was at least 10% less frequent.

| | Position | | | | | | |
|---|---|---|---|---|---|---|---|
| Sample | 7 Mod (%) | 6 Mod (%) | 5 Mod (%) | 4 Mod (%) | 3 Mod (%) | 2 Mod (%) | 1 Mod (%) |
| Library | C12 (19.3) | T (20.0) | C12 (19.3) | G (20.8) | Nap (22.9) | C12 (28.8) | G (25.9) |
| Library* | C12 (18.1) | T (20.2) | Phe (18.6) | C12 (20.2) | Nap (23.0) | C12 (29.4) | G (25.4) |
| 1$^{st}$ TBA elution | T (32.7) | T (76.1) | C12 (23.6) | C12 (29.7) | Phe (30.5) | T (74.8) | Nap (34.9) |
| 1$^{st}$ TBA elution* | T (31.2) | T (73.3) | Phe (23.9) | C12 (30.4) | T (28.7) | T (72.2) | Nap (26.9) |
| 2$^{nd}$ TBA elution | G (31.9) | T (61.8) | C12 (32.5) | C12 (31.2) | Phe (25.8) | T (59.5) | Nap (31.5) |
| 2$^{nd}$ TBA elution* | Trp (26.2) | T (61.5) | C12 (25.1) | C12 (29.8) | T (26.0) | T (59.3) | Nap (26.9) |
| Thrombin elution | C12 (29.3) | T (23.8) | C12 (25.2) | Nap (24.3) | Nap (34.0) | C12 (27.1) | Nap (25.2) |
| Thrombin elution* | C12 (29.0) | T (21.9) | C12 (28.0) | Nap (29.4) | Nap (42.9) | C12 (32.7) | Nap (29.0) |

Since each position of the combinatorial library had six possible options, an unbiased sample would show each modification occurring in 16.67% of all sequences of a sample for a given position. As is shown in the above table, some modifications in samples that underwent selection were heavily favoured (up to 76.1%). T is strongly favoured in positions 6 and 2, C12 is strongly favoured in positions 5 and 4, and Nap is strongly favoured in position 1. This type of data complements that of Table 7, as there is information on individual sequences as well as single site modifications that may help design better binding aptamers. Interestingly, although Phe was prominent in the most popular sequences there was only a minor observed positional preference for Phe in position 3. The library samples did indicate some level of bias as there were some positions with unusually high representations of modifications, such as position 2 with C12 at ~29%. C12 in fact showed up often as the most popular modification in the library, suggesting a more favourable coupling of the phosphoramidite in question.

EXAMPLE IV

Binding Affinity and Serum Ability of Aptamer Candidates

Figure 12A:
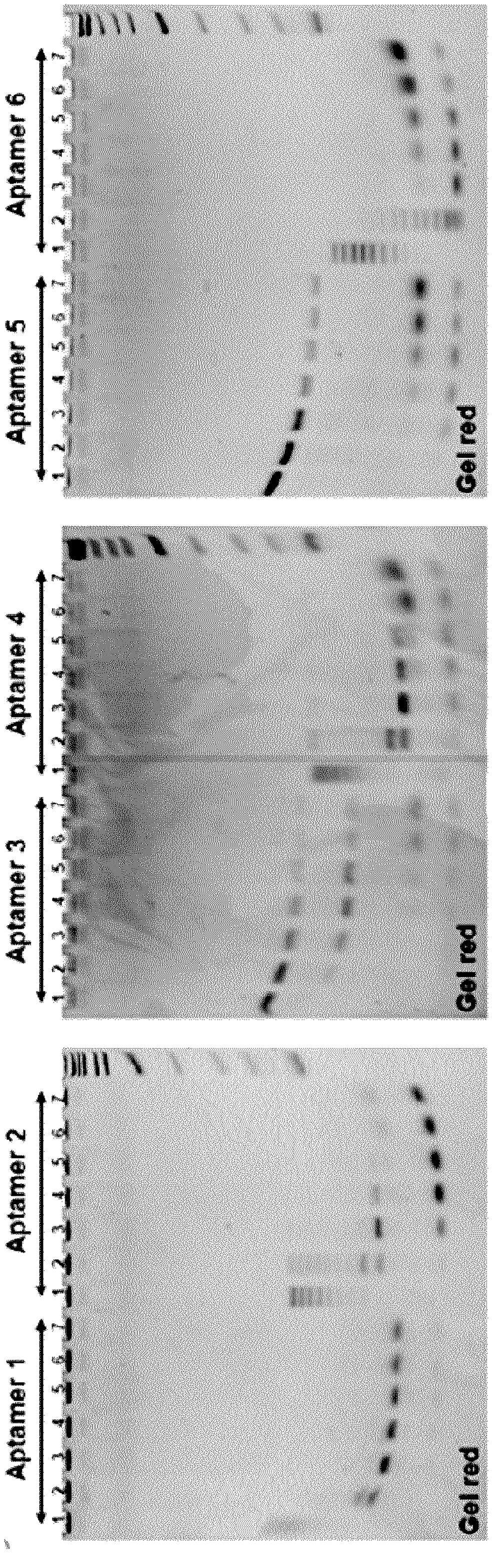
FIG. 12 shows gel electrophoresis of the serum stability measured in terms of half-life using denaturing gel electrophoresis for 6 aptamers. Aptamer1: 5' FAM GG TT GG PheGT GG TT GG T 3', Aptamer2: 5' FAM GG TrpT GG PheC12T GG TT GG G 3', Aptamer3: 5' FAM GG GT GG PheC12T GG PheT GG Nap 3', Aptamer4: 5' FAM GG TT GG TC12T GG TT GG T 3', Aptamer5: 5' FAM GG TT GG TGT GG TT GG Nap 3', Aptamer6: 5' FAM GGTTGGTGTGGTTGG, at time points 1: 2 mins, 2: 1 h, 3: 3 h, 4: 6.5 h, 5: 10 h, 6: 19.5 h, 7: 24 h, for gel red (FIG. 12A) and fluorescein (FIG. 12B).
Figure 12B:
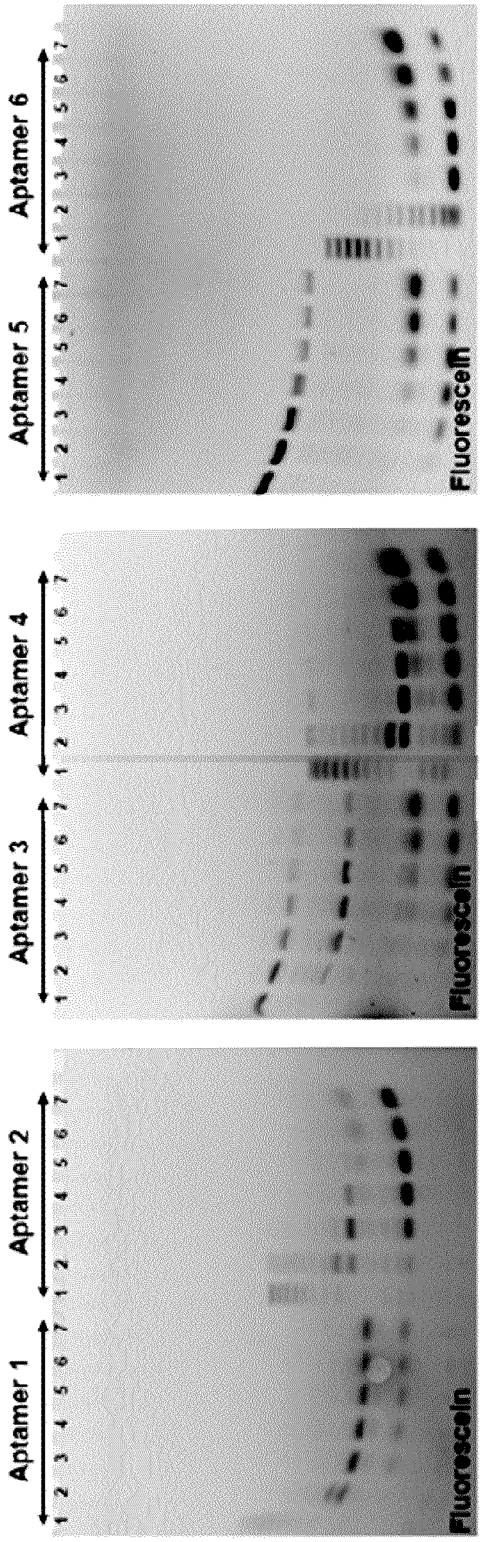

Based on the quantitative and qualitative results from sequencing, the following aptamers in Table 9 were selected as potential strong binding candidates and were synthesized without any branching unit, primers or DNA barcodes for binding affinity studies. 5' 6-carboxyfluorescein phosphoramidite was appended to the aptamers to enable fluorescence anisotropy measurements of binding affinity and serum stability measurements. Aptamers were chosen based on both the popularity of individual sequences and the prevalence of a monomer in a specific position across all sequences of a given sample. Serum stability was measured in terms of half-life using denaturing gel electrophoresis (FIG. 12A and FIG. 12B). Aptamer1 had a single site modification of the TBA based on the presence of Phe at position 5 in the ten most popular individual sequences of different samples. Aptamer4 and Aptamer5 were single site modifications of the TBA based on the popularity of positional modifications across all sequences, which showed strong preferences for Nap at position 1 and C12 at position 4. Aptamer2 and Aptamer3 were based on the popularity of individual sequences, with both appearing frequently in the samples that had undergone selection.

TABLE 9

Binding affinities and serum stability of aptamer candidates.

| Aptamer | Condensed Sequence (5' to 3') | | | | | | | Binding Affinity (nmol) | Serum Stability (h) |
|---|---|---|---|---|---|---|---|---|---|
| TBA | T | T | T | G | T | T | T | 11 ± 8 | <0.3 |
| Aptamer1 | T | T | Phe | G | T | T | T | 26 ± 4 | <0.3 |
| Aptamer2 | Trp | T | Phe | C12 | T | T | G | 10 ± 5 | <0.3 |
| Aptamer3 | G | T | Phe | C12 | Phe | T | Nap | 6 ± 4 | 5.0 |
| Aptamer4 | T | T | T | G | T | T | Nap | 24 ± 4 | 4.5 |
| Aptamer5 | T | T | T | C12 | T | T | T | 37 ± 5 | <0.3 |

Binding affinities of the modified aptamers were comparable to that of the unmodified aptamer, but notably Aptamer3 showed improved binding. Aptamer3 and Aptamer5 both had increased half-lives in serum, likely as a result of the added stability imparted by the 3' Nap modification. Aptamer2 and Aptamer3 that were directly identified from the screening were further analysed using Microscale Thermophoresis (2Bind) and were measured in the presence of 0.1 mg/mL sheared salmon sperm DNA to check for specific interaction with the target thrombin. Again Aptamer3 displayed superior binding properties in comparison to the original unmodified aptamer TBA (Table 10) suggesting the novel aptamer displays between 2 and 6 fold improved affinity.

TABLE 10

Validating the binding affinities of the best aptamer candidates.

| Aptamer | Binding Affinity by MST (nmol) (N = 2) | Binding Affinity by FA with salmon sperm DNA (nmol) (N = 3) |
|---|---|---|
| TBA | 126 ± 1 | 12 ± 2 |
| Aptamer2 | (not tested) | 10 ± 6 |
| Aptamer3 | 20 ± 14 | 5 ± 4 |

Aptamer2 and Aptamer3 were further analyzed in head-to-head studies with TBA to confirm improved binding properties. First the fluorescence anisotropy assay was repeated, as described above but with the addition of 0.1 mg/mL of sheared salmon sperm DNA to reduce non-specific binding. Next, Aptamer3 and TBA were sent to 2Bind Gmbh and were tested using the microscale thermophoresis assay. The aptamers were used at 100 nM, thrombin was titrated down in 16 steps in 1:1 dilution with buffer starting from 1.53 μM. Buffer was the same as all experiments with the exception of Triton-X (20 mM Tris, 140 mM NaCl, 20 mM KCl, 1 mM CaCl2, 1 mM MgCl2, 0.1% Triton X). MST analysis was performed using a Monolith NT.115 Pico (Blue-nano) instrument.

EXAMPLE V

Cellular Uptake of Modified Alenomers

Figure 13:
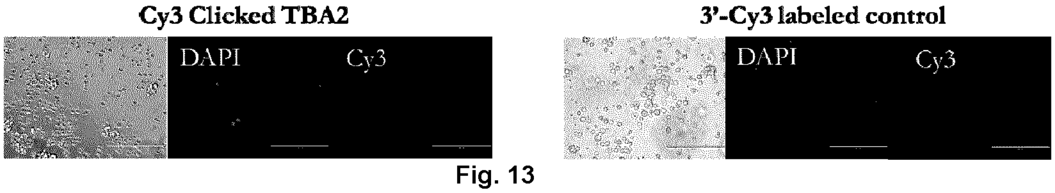
FIG. 13 shows microscopy images of HEK293 cells treated with alenomers vs DNA for 24 hours in the absence of serum showed stronger Cy3 fluorescence.

While thrombin aptamers and some alenomers targeting thrombin would not to undergo cellular uptake, future therapeutic applications of alenomers may indeed be enhanced by improved cellular uptake. As such, TBA2 was modified, which included the primer, DNA code, and thymidine linker, with a Cy3 dye by clicking an azide-Cy3 onto the alkyne handle. As a comparison, a DNA with a similar molecular weight with a 3'-modified Cy3 was used: ATCGGGTGTGGGTGGCGTAAAGGGAG-CATCGGACAAAAAAAAAGCCACCCAAA/3 Cy5Sp/ (SEQ ID NO: 28). 500 nM of the TBA2 alenomer and the control DNA was separately incubated with Hek293 cells in media (absence of serum) for 24 h. Cells were thoroughly washed with PBS (×4) to remove remaining DNA or DNA interacting with the cell membranes, then placed on a glass slide for imaging. Fluorescent images (FIG. 13) of the cells (20× magnification) indicate stronger fluorescence in the TBA2 alenomer treated cells compared to the 3'-labelled unmodified DNA, with no increase in cell death (DAPI stained cells) suggesting improved cellular uptake.

EXAMPLE VI

Compatibility of Unnatural Monomers with Hydrazine Deprotection

Figure 14:
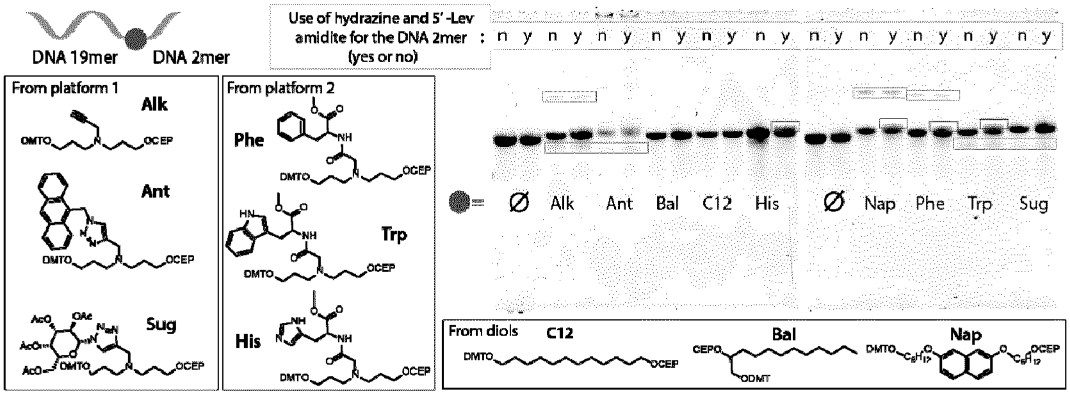
FIG. 14 shows results of the synthesis of modified DNA 21mers and the analysis of hydrazine influence. Crude mixture post-SPS and deprotection were analyzed through 15% PAGE in denaturing conditions. For each modification, lanes with a 'y' contain strands tested with hydrazine and 5'-Lev amidite while lanes with a 'n' were made following a standard protocol. Frames directly above the dark bands were negligible amounts of byproducts hypothesized to be present because of hydrazine treatments. Frames more removed from the dark bands (above or below) were negligible amounts of byproducts hypothesized to be from coupling step of the unnatural monomer. In all cases, coupling efficiency was found to be >90%.

The high yielding incorporation of the 9 unnatural monomers (Alk, Ant, Bal, C12, His, Phe, Nap, Sug, Trp) at internal positions of a DNA strand was confirmed and their compatibility with hydrazine through the following experiment (FIG. 14). The 9 phosphoramidites were coupled to model DNA 19mers on solid support. After the capping and oxidation steps, the solid support was divided into two aliquots. The first one underwent 10 hydrazine treatments before deblocking the 5'-DMT protecting group. Then, the coupling of a 5'-Levulinyl followed by 10 other hydrazine treatments and a 5'-DMT phosphoramidite coupling were performed. The DNA strands on the CPG of the second aliquot underwent similar reactions except that no hydrazine treatment nor 5'-Lev phosphoramidites were involved. An unmodified strand was also synthesized using the same conditions. Crude mixtures were analyzed by gel electrophoresis (FIG. 14). Very small amounts (<10%) of potential dimers visible in lanes Alk, Nap and Phe and of unmodified DNA 19mer visible in lanes Alk, Ant, Trp and Sug were found proving the high coupling efficiency of each phosphoramidite. For hydrazine-treated strands, lanes Nap, Phe and Try showed a light band on top of the expected product band which may be due to unwanted branched oligomers. The amount of such byproducts was negligible under the specific conditions tested, meaning the phosphoramidites were adapted to the branched oligomer synthetic conditions.

EXAMPLE VII

Positional Tendencies

Table 11 below shows data for the least popular modifications, with bolded entries being at least 10% less common than any other modification. There was some library bias evidenced by the entries in the library rows of Table 11, as certain modifications are present at levels well below the ideal 16.7%. Often, the least common modifications in the library samples translated to the least common modifications in the samples that underwent screening, such as with His in position 6, C is position 3 and A in position 2.

Nevertheless, this data does still provide information on which monomers are least well suited to a given position. The Sug modification, for instance, is overwhelmingly unfavourable in positions 7 and 1.

TABLE 11

The relative frequency (in %) of the least observed modification (mod) at a certain position across all sequences from a given sample. Asterisks (*) indicate the library undergoing selection was fluorescently tagged.

| | Position | | | | | | |
|---|---|---|---|---|---|---|---|
| Sample | 7 Mod (%) | 6 Mod (%) | 5 Mod (%) | 4 Mod (%) | 3 Mod (%) | 2 Mod (%) | 1 Mod (%) |
| Library | Ant (14.7) | His (9.7) | Sug (11.8) | Alk (12.7) | C (5.7) | A (6.7) | C12 (5.4) |
| Library* | Ant (13.5) | His (10.7) | Sug (12.0) | Sug (12.2) | C (6.0) | A (6.9) | C12 (6.4) |
| $1^{st}$ TBA wash | Sug (3.1) | His (2.1) | Sug (9.6) | Alk (10.6) | C (1.3) | A (1.4) | Sug (4.4) |
| $1^{st}$ TBA wash* | Sug (3.2) | His (2.4) | T (9.5) | Alk (10.2) | C (1.4) | A (1.3) | Sug (8.5) |
| $2^{nd}$ TBA wash | Sug (5.1) | His (3.9) | Sug (7.6) | Alk (8.4) | Ant (6.2) | A (1.8) | Sug (4.4) |
| $2^{nd}$ TBA wash* | Ant (4.5) | His (3.6) | T (8.6) | A (8.0) | C (1.8) | A (1.7) | Sug (7.7) |
| Thrombin wash | Sug (10.9) | His (8.8) | Sug (9.7) | A (9.4) | C (3.5) | A (5.8) | Sug (5.6) |
| Thrombin wash* | Sug (11.9) | His (8.8) | T (9.4) | Sug (8.1) | C (3.6) | A (5.1) | Sug (5.8) |

While the present disclosure has been described in connection with specific embodiments thereof, it will be understood that it is capable of further modifications and is intended to cover any variations, uses, or adaptations, including such departures as come within known or customary practice within the art and as may be applied to the essential features hereinbefore set forth, and as follows in the scope of the appended claims.

What is claimed is:

1. A method of preparing aptamer-like encoded oligomer (ALEnOmer), said method comprising:

a) attaching a branching unit at the 5' end of a first DNA branch attached to a solid support for generating a second branch linked to the first branch by the branching unit;

b) extending in parallel the first branch by coupling at least one nucleotide with an orthogonal protecting group and the second branch by coupling at least one phosphoramidite monomer with an orthogonal protecting group, wherein the extension of the second branch producing an oligomer;

c) separating the solid support into a number of aliquots of solid supports;

d) incorporating at least one phosphoramidite building block on the second branch and at least one DNA codon of the second branch building block at the 5' end of the first branch;

e) pooling the aliquots of solid supports together;

g) cleaving the ALEnOmer from the solid support and deprotecting the ALEnOmer; and f) isolating and purifying the full-length ALEnOmer.

2. The method of claim 1, comprising a first step a') of synthesizing the first DNA branch by solid phase synthesis.

3. The method of claim 1, wherein a linker is added to the second branch.

4. The method of claim 1, wherein the linker comprises a fluorescent label.

5. The method of claim 1, wherein the at least one monomer protecting group or the at least one nucleotide orthogonal protecting group is dimethoxytrityl (DMT), monomethoxytrityl (MMT), or levulinyl.

6. The method of claim 1, wherein the first branch and second branch are extended by coupling a 5' dimethoxytrityl (5'-DMT) followed by coupling a 5'-levulinyl phosphoramidite.

7. The method of claim 1, wherein the oligomer has a degree of polymerization of at least 5, of at least 8, or has a degree of polymerization of >15.

8. The method of claim 1, wherein the at least one nucleotide orthogonal protecting group is incorporated on the second branch and the at least one monomer phosphoramidite orthogonal protecting group on the first branch.

9. The method of claim 1, wherein the oligomer is an aptamer.

10. The method of claim 9, wherein the aptamer comprises at least one unnatural monomer.

11. The method of claim 10, wherein the unnatural monomer is at least one of a phosphoramidite monomer Alk, an anthracene modification (Ant), a phosphoramidite monomer Bal, a phosphoramidite monomer C12, an histidine-like modification (His), a phenylalanine modification (Phe), a Naphthalene (Nap), a carbohydrate-containing modification (Sug), and a tryptophan-like modification (Trp).

12. The method of claim 1, said method comprising repeating steps d), e) and f) n times producing a library of ALEnOmers.

* * * * *